(12) United States Patent
Michelson

(10) Patent No.: US 8,262,736 B2
(45) Date of Patent: *Sep. 11, 2012

(54) RADIALLY EXPANDING IMPLANTS

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2048 days.

This patent is subject to a terminal disclaimer.

(21) Appl. No.: 11/268,168

(22) Filed: Nov. 7, 2005

(65) Prior Publication Data

US 2006/0058878 A1  Mar. 16, 2006

Related U.S. Application Data

(63) Continuation of application No. 10/105,839, filed on Mar. 25, 2002, now Pat. No. 7,128,760.

(60) Provisional application No. 60/279,205, filed on Mar. 27, 2001, provisional application No. 60/281,714, filed on Apr. 4, 2001.

(51) Int. Cl.
    *A61F 2/44* (2006.01)
(52) U.S. Cl. .................................... 623/17.16
(58) Field of Classification Search .... 623/17.11–17.16; 411/60.1, 60.2, 55, 71, 72, 45–50
See application file for complete search history.

(56) References Cited

U.S. PATENT DOCUMENTS

| | | | |
|---|---|---|---|
| 332,701 A * | 12/1885 | Craig | ............................... 411/55 |
| 4,309,777 A | 1/1982 | Patil | |
| 4,501,269 A | 2/1985 | Bagby | |
| 4,607,992 A * | 8/1986 | Mauritz et al. | ................... 411/45 |
| 4,810,141 A * | 3/1989 | Rainville | ........................ 411/38 |
| 4,878,915 A | 11/1989 | Brantigan | |
| 4,961,740 A | 10/1990 | Ray et al. | |
| 5,015,247 A | 5/1991 | Michelson | |
| 5,026,373 A | 6/1991 | Ray et al. | |
| 5,055,104 A | 10/1991 | Ray | |
| 5,059,193 A | 10/1991 | Kuslich | |
| 5,123,926 A | 6/1992 | Pisharodi | |
| 5,147,402 A | 9/1992 | Bohler et al. | |
| 5,192,327 A | 3/1993 | Brantigan | |
| 5,263,953 A | 11/1993 | Bagby | |
| 5,290,312 A | 3/1994 | Kojimoto et al. | |
| 5,306,310 A | 4/1994 | Siebels | |
| 5,390,683 A | 2/1995 | Pisharodi | |
| 5,439,684 A | 8/1995 | Prewett et al. | |
| 5,484,437 A | 1/1996 | Michelson | |
| 5,549,679 A | 8/1996 | Kuslich | |
| 5,554,191 A | 9/1996 | Lahille et al. | |
| 4,961,740 A | 1/1997 | Ray et al. | |
| 5,609,635 A | 3/1997 | Michelson | |
| 5,609,636 A | 3/1997 | Kohrs et al. | |
| 5,653,763 A | 8/1997 | Errico et al. | |
| 5,665,122 A | 9/1997 | Kambin | |

(Continued)

FOREIGN PATENT DOCUMENTS

DE           44 16 605           6/1995

(Continued)

*Primary Examiner* — Anu Ramana
(74) *Attorney, Agent, or Firm* — Martin & Ferraro, LLP

(57) ABSTRACT

Orthopedic implants being at least in part radially expandable at one of the leading or trailing ends to expand both the height and at least a portion of the width of the implant, and instruments and methods for inserting the implants into an implantation space are disclosed.

23 Claims, 25 Drawing Sheets

U.S. PATENT DOCUMENTS

| | | |
|---|---|---|
| 5,693,100 A | 12/1997 | Pisharodi |
| 5,702,391 A | 12/1997 | Lin |
| 5,713,904 A | 2/1998 | Errico et al. |
| 5,749,916 A | 5/1998 | Richelsoph |
| 5,776,199 A | 7/1998 | Michelson |
| 5,782,832 A | 7/1998 | Larsen et al. |
| 5,865,848 A | 2/1999 | Baker |
| 5,928,242 A | 7/1999 | Kuslich et al. |
| 5,928,284 A | 7/1999 | Mehdizadeh |
| 5,968,098 A | 10/1999 | Winslow |
| 5,976,187 A | 11/1999 | Richelsoph |
| 5,980,522 A | 11/1999 | Koros et al. |
| 6,015,436 A | 1/2000 | Schonhoffer |
| 6,019,792 A | 2/2000 | Cauthen |
| 6,039,761 A | 3/2000 | Li et al. |
| 6,045,579 A | 4/2000 | Hochshuler et al. |
| 6,059,829 A | 5/2000 | Schlapfer et al. |
| 6,080,155 A | 6/2000 | Michelson |
| 6,080,193 A | 6/2000 | Hochshuler et al. |
| 6,083,225 A | 7/2000 | Winslow et al. |
| 6,093,207 A | 7/2000 | Pisharodi |
| 6,102,950 A | 8/2000 | Vaccaro |
| 6,117,174 A | 9/2000 | Nolan |
| 6,126,689 A | 10/2000 | Brett |
| 6,129,763 A | 10/2000 | Chauvin et al. |
| 6,176,882 B1 | 1/2001 | Biedermann et al. |
| 6,183,517 B1 | 2/2001 | Suddaby |
| 6,190,414 B1 | 2/2001 | Young et al. |
| 6,193,757 B1 | 2/2001 | Foley et al. |
| 6,201,039 B1 | 3/2001 | Brown et al. |
| 6,210,412 B1 | 4/2001 | Michelson |
| 6,419,705 B1 | 7/2002 | Erickson |
| 6,436,140 B1 | 8/2002 | Liu et al. |
| 6,443,989 B1 | 9/2002 | Jackson |
| 6,451,057 B1 | 9/2002 | Chen et al. |
| 6,454,806 B1 | 9/2002 | Cohen et al. |
| 6,821,298 B1 | 11/2004 | Jackson |
| 6,896,680 B2 | 5/2005 | Michelson |
| 6,986,772 B2 | 1/2006 | Michelson |
| 7,128,760 B2 | 10/2006 | Michelson |
| 7,410,501 B2 | 8/2008 | Michelson |
| 7,445,636 B2 | 11/2008 | Michelson |

FOREIGN PATENT DOCUMENTS

| | | | |
|---|---|---|---|
| EP | 0 664 994 | | 8/1995 |
| FR | 2 782 632 | | 3/2000 |
| SU | 1424826 A1 | | 9/1988 |
| WO | WO 97/00054 | | 1/1997 |
| WO | WO 98/48739 | | 11/1998 |
| WO | WO 99/07312 | | 2/1999 |
| WO | WO 99/42062 | | 8/1999 |
| WO | WO 00/12033 | | 3/2000 |
| WO | WO 0012033 | * | 3/2000 |
| WO | WO 00/35388 | | 6/2000 |
| WO | WO 00/35389 | | 6/2000 |
| WO | WO 00/74605 | | 12/2000 |
| WO | WO 00/78253 | | 12/2000 |

* cited by examiner

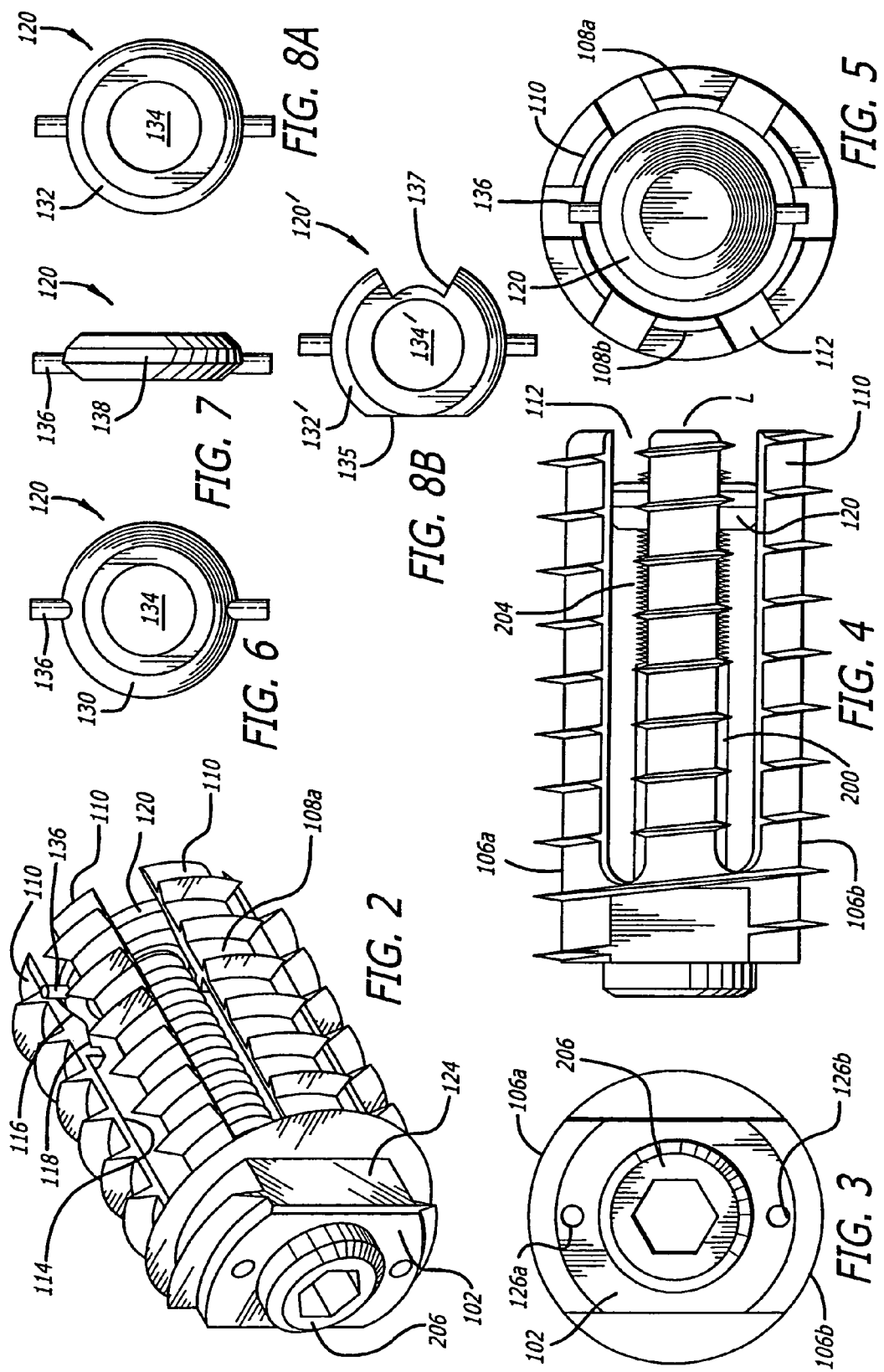

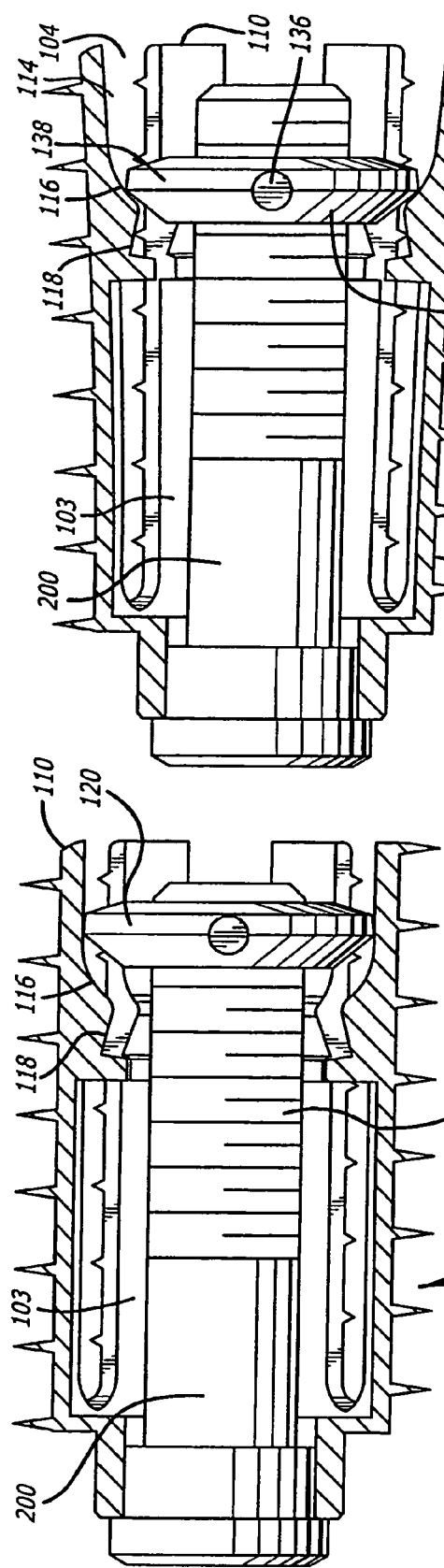
FIG. 9
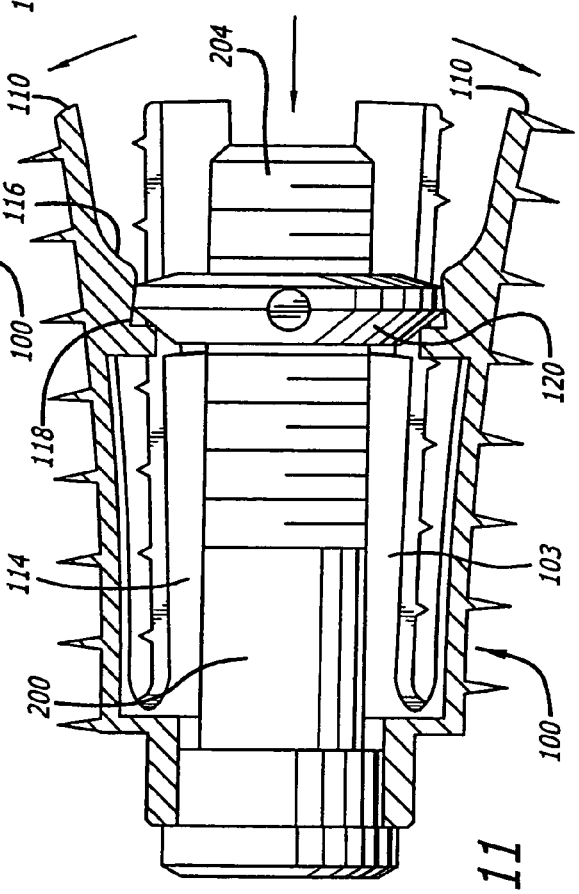
FIG. 10
FIG. 11

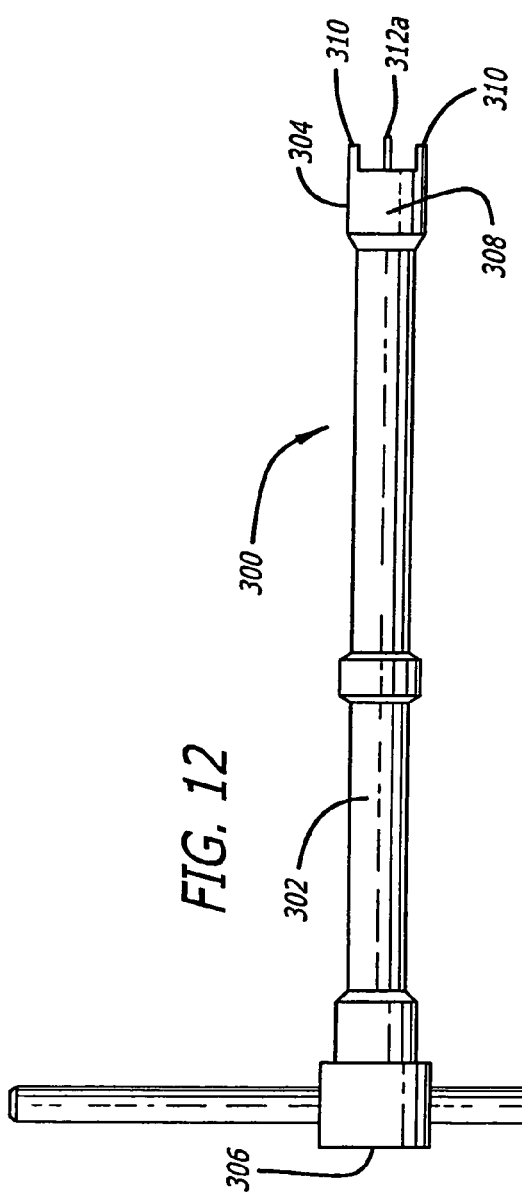
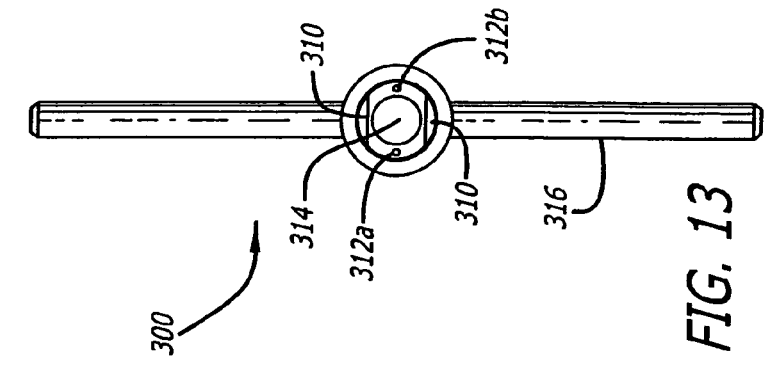
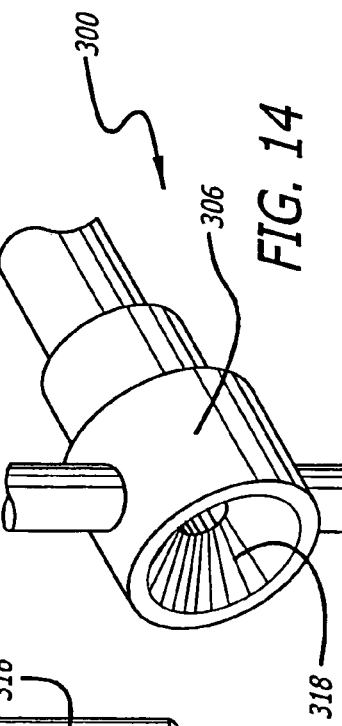
FIG. 12
FIG. 13
FIG. 14
FIG. 15

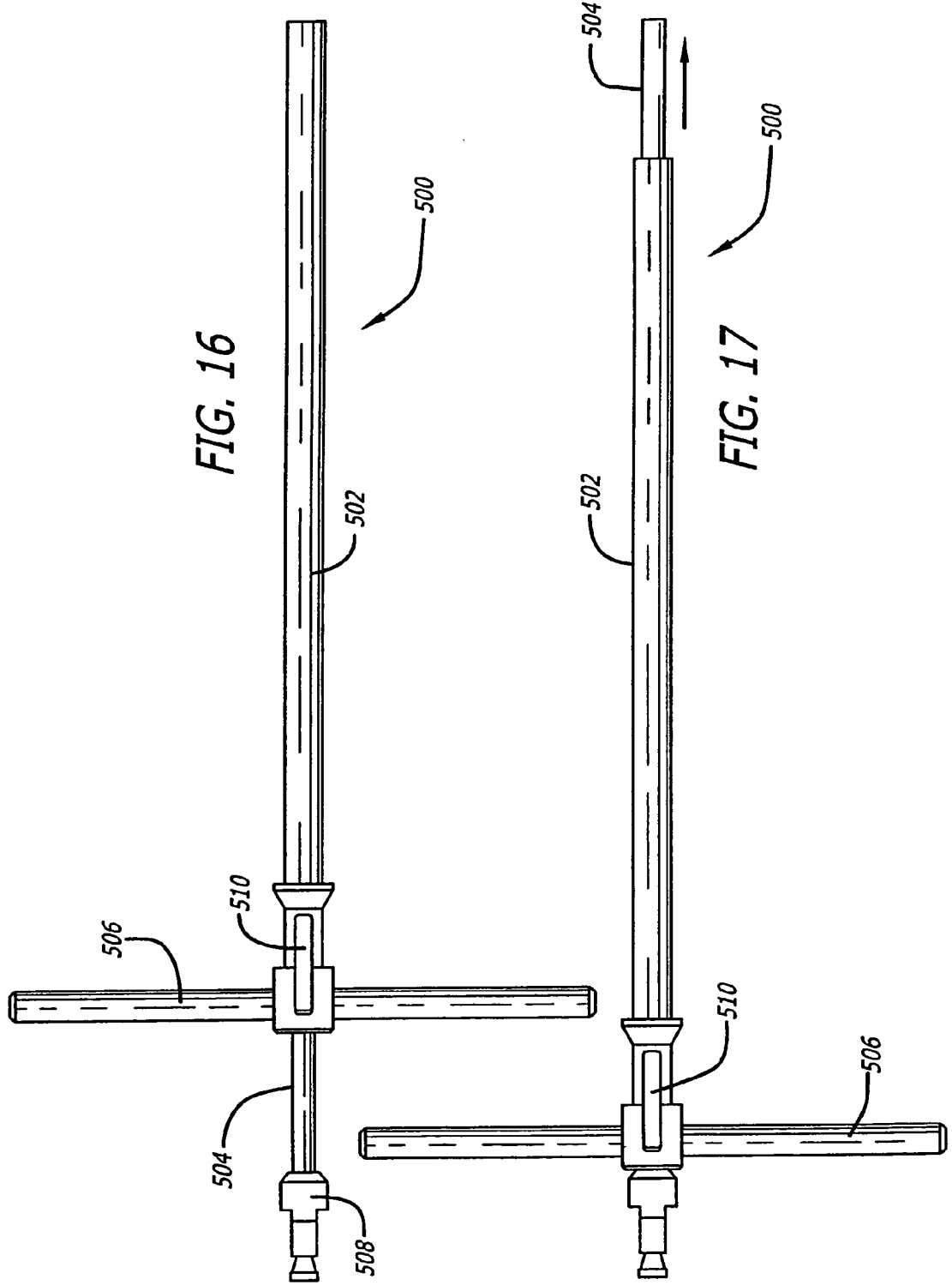

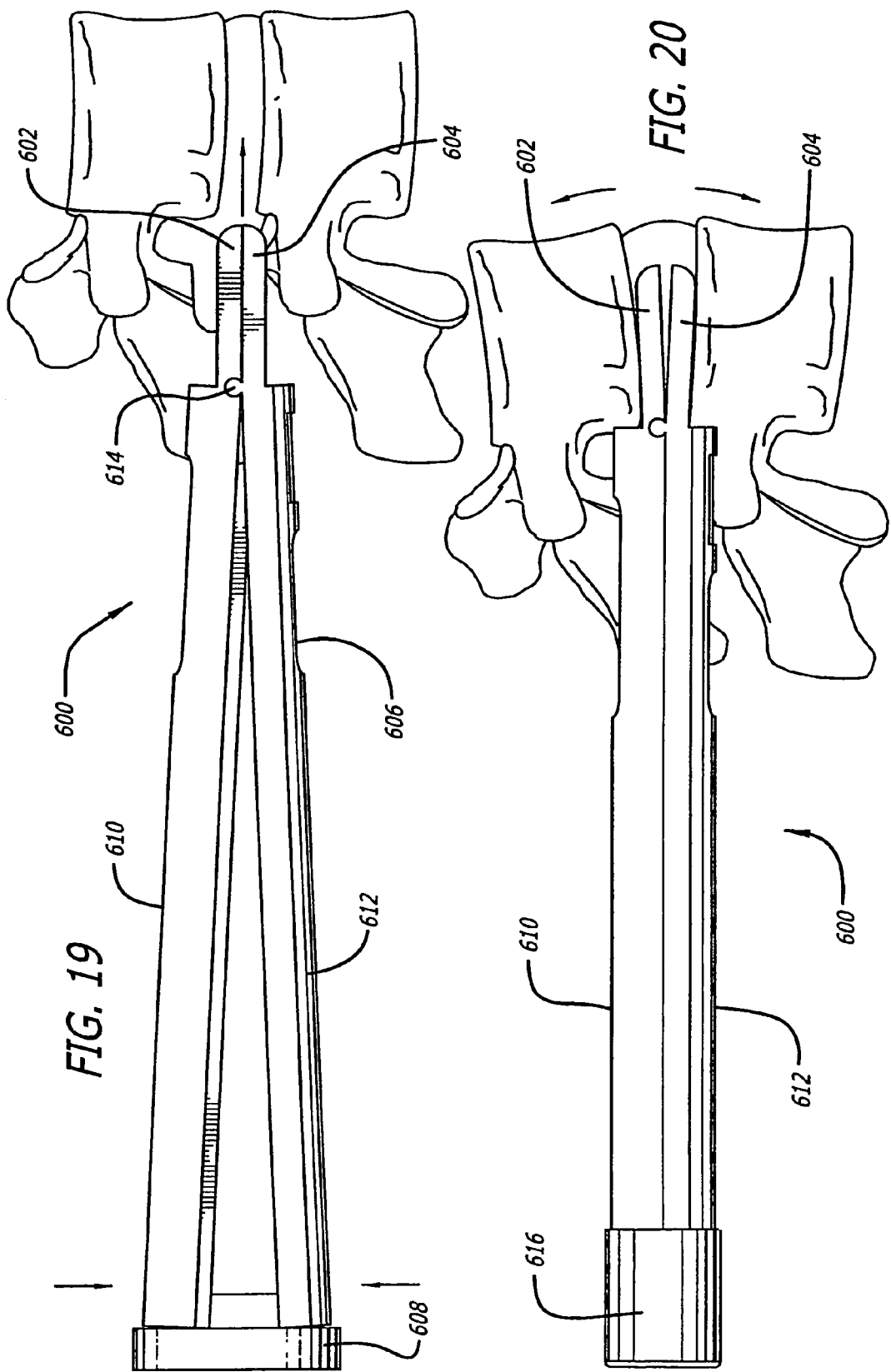

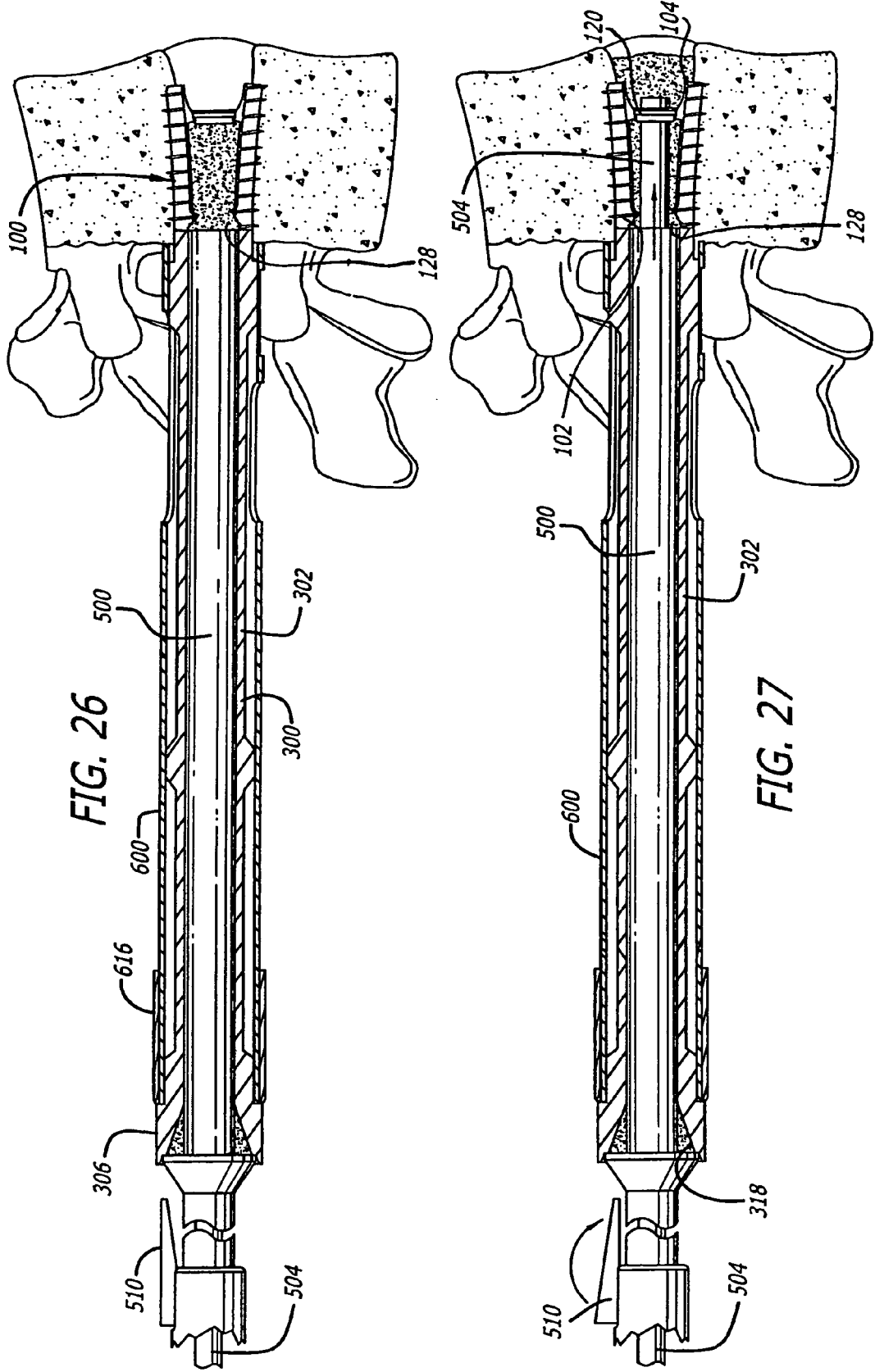

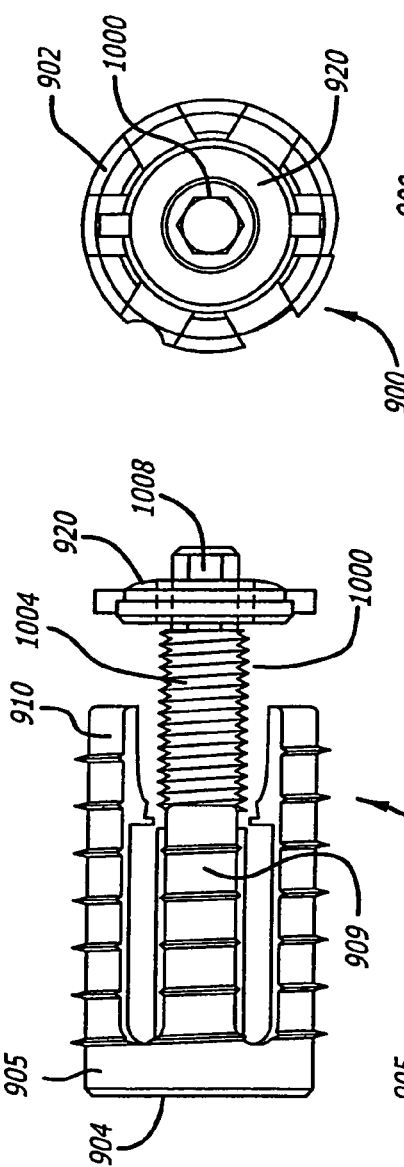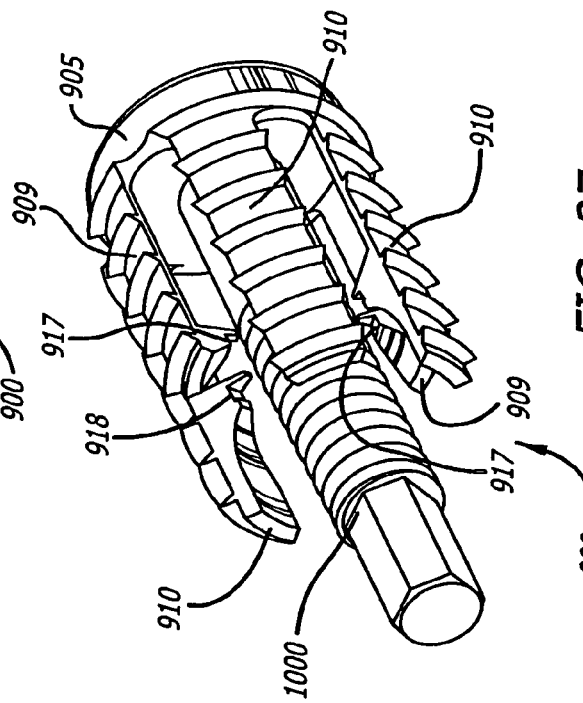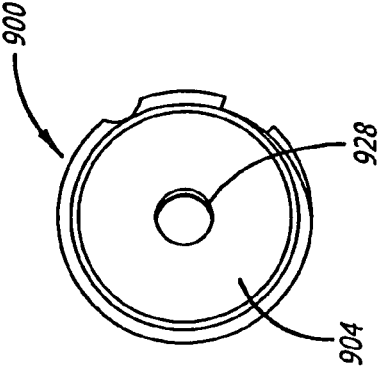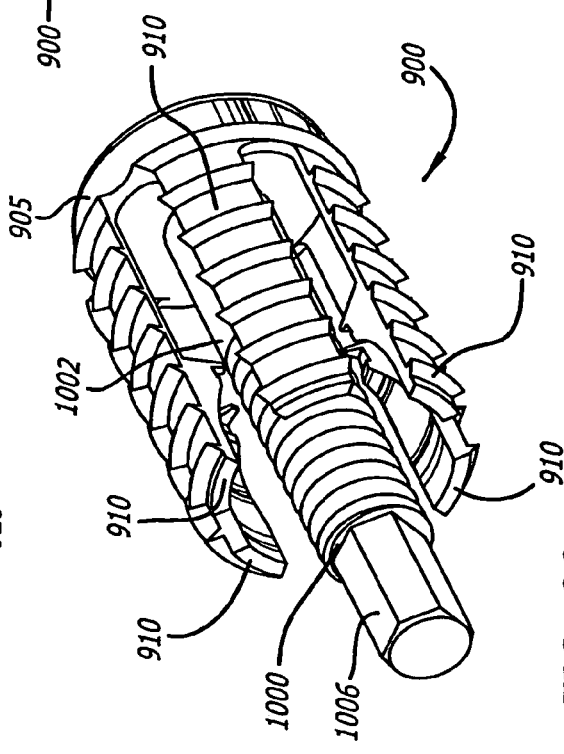

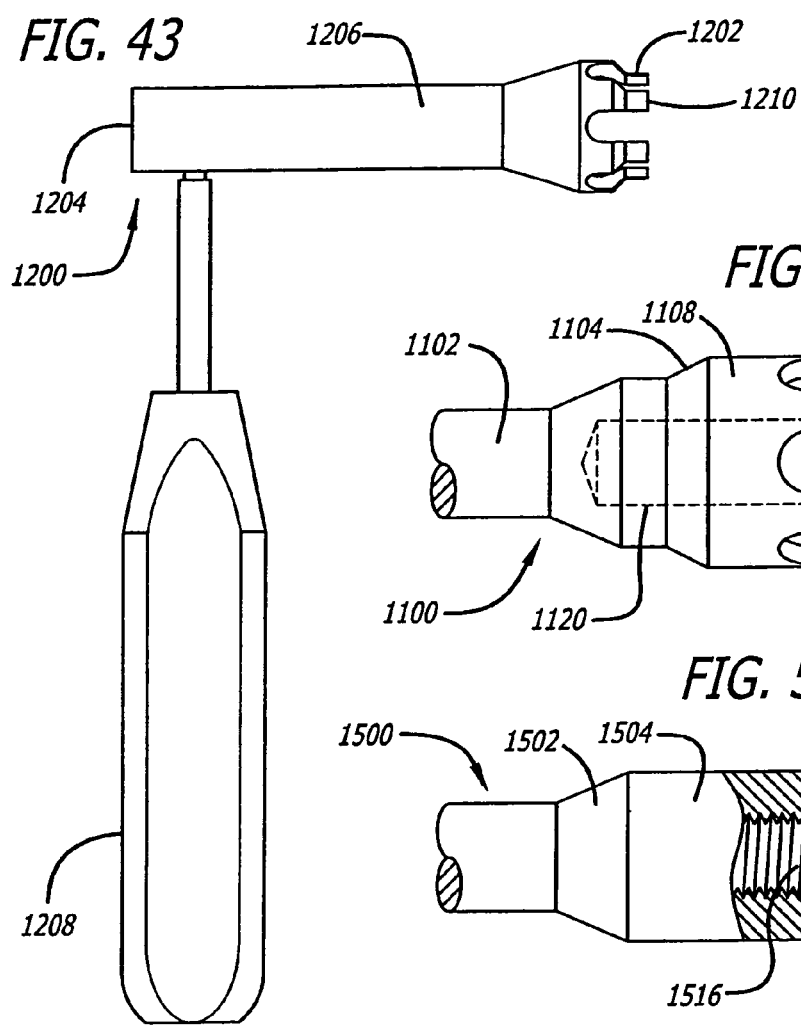

RADIALLY EXPANDING IMPLANTS

RELATED APPLICATIONS

This application is a continuation of application Ser. No. 10/105,839, filed Mar. 25, 2002 now U.S. Pat. No. 7,128,760; which claims benefit of provisional Application No. 60/279,205, filed Mar. 27, 2001; and provisional Application No. 60/281,714, filed Apr. 4, 2001; all of which are incorporated by reference herein.

BACKGROUND OF THE INVENTION

1. Field of the Invention

The present invention relates generally to interbody spinal implants, and instruments and methods for inserting interbody spinal implants into an implantation space in the spine, and in particular to an expandable interbody (for placement at least in part between adjacent vertebral bodies in the space previously occupied by disc material) spinal fusion implants for the immobilization of adjacent vertebrae.

2. Description of the Related Art

Expandable spinal fusion implants have height raising capabilities that are utilized once the implant is initially positioned. Such height raising capability may be utilized within the spine anteriorly, posteriorly, or both and to various extents, respectively to raise the front or back of the implant. More particularly, such implants have upper and lower surfaces of upper and lower portions that in an insertion position are collapsed relative to one another and in a deployed position are spaced further away from one another than in the collapsed position.

Expandable fusion implants offer the advantage of allowing for the placement of a potentially larger implant through a smaller opening in a patient's body. The first expandable spinal fusion (allowing for the growth of bone from vertebral body to vertebral body through the implant) implant was invented by Michelson and also is disclosed in U.S. Pat. No. 5,776,199, filed Jun. 28, 1988, which is hereby incorporated by reference herein.

Expandable interbody spinal fusion implants preferably may be inserted from an anterior approach to the spine, an approach posterior to the vertebral transverse processes, or to either side of the spinal midline in pairs. Such expandable implants are adapted to increase in height at their leading ends or at their trailing ends from a collapsed state to an expanded state for the purpose of increasing spinal lordosis at that interspace. During installation of expandable interbody spinal fusion implants, it is desirable that the surgeon have the ability to precisely control the implant with the appropriate instruments and methods to load the implant with appropriate bone growth promoting material, to insert the implant into the implantation space, to deploy the implant to a final expanded state, and to further load the implant with bone growth material if so desired.

Also known in the art are expandable interbody spinal fusion implants that are circumferentially expandable at one of their leading or trailing ends to expand both the height and the width of the implant. Such implants have an expansion mechanism that is moved from the trailing end through the interior of the implant to reach the leading end to expand the implant. Any bone growth material present within the interior of the implant would be forced out of the interior of the implant by the expansion mechanism passing therethrough. Accordingly, such implants cannot be effectively preloaded with bone growth promoting material prior to expansion of the implant.

There exists a need for a circumferentially expanding implant that is substantially hollow and substantially devoid of any elaborate or substantial space occupying expansion mechanism to permit preloading of the implant with bone growth promoting material prior to expansion of the implant. The expansion mechanism would not interfere with the capacity to compressively load osteogenic material such as bone or any other suitable material through the length of the implant and to have it extrude from the implant. The extrusion of the osteogenic material from the implant provides an increased volume of osteogenic material over a greater surface area of the adjacent vertebral bodies adjacent the disc space to be fused and beyond the surface area of contact of the implant to the vertebral bodies themselves. Surrounding the implant itself with additional fusion promoting substances in contact with the adjacent vertebral bodies may enhance the fusion process.

There also exists a need for instruments and methods for use with expandable interbody spinal fusion implants providing for all of the aforementioned needs individually or in combination.

SUMMARY OF THE INVENTION

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The present invention is directed to an interbody spinal fusion implant particularly adapted for anterior, posterior, and posterior lateral interbody spinal fusion; and methods and instrumentation for a preferred insertion of these implants.

The present invention implant is adapted to have a generally constant size at one end while allowing for a generally circumferential increase in size at the opposite end. This feature is particularly useful for posterior lumbar interbody fusion and posterior lateral interbody spinal fusion, where it is desirable to have the vertebral bodies spaced apart more anteriorly than posteriorly to restore the lumbar lordosis. The implant is preferably inserted in a generally cylindrical form or more particularly with the opposed surfaces of the implant adapted to contact each of the opposed adjacent vertebral bodies adjacent to the disc space to be fused being generally parallel. Subsequently, the implant is expanded at the leading end so that the opposed vertebral body engaging surfaces of the implant are then in a generally angular relationship to each other over a substantial portion of the length of the implants. The present invention methods and instrumentation in conjunction with the present invention implant allows for the installation of an implant that in its final implanted form is substantially hollow with the exception of an expander ring which is itself preferably hollow so as to not interfere with the full loading of the implant and the extrusion there through of the selected osteogenic material.

In accordance with the purposes of the present invention, as embodied and broadly described herein, an interbody spinal fusion implant is provided for implantation from at least in part a posterior approach at least in part within and across the height of a disc space between two adjacent vertebral bodies of an adult human spine. The implant includes a body having a leading end for insertion first into the disc space, a trailing end opposite the leading end, and a mid-longitudinal axis along the length of the body. The body has an upper portion adapted to contact one of the adjacent vertebral bodies, a lower portion opposite the upper portion adapted to contact another one of the adjacent vertebral bodies, and at least one side portion between the upper and lower portions. Each of the upper, lower, and side portions extend from the trailing end of the body and are spaced apart from one another to form a hollow interior therebetween. The hollow interior is configured to hold at least some bone growth promoting material therein. The upper and lower portions are configured to permit for the growth of bone from adjacent vertebral body to adjacent vertebral body through the body of the implant. Each of the upper, lower, and side portions are configured to move at least in part in a direction away from the mid-longitudinal axis of the body to allow for expansion of the height and at least a portion of the width of the body. The upper, lower, and side portions have a collapsed position relative to one another allowing for a collapsed height and width of the body, and an expanded position relative to one another allowing for an expanded height and width of the body. The expanded height and width of the body is greater than the collapsed height and width of the body, respectively.

The implant also includes an expander positioned at least in part within the hollow interior. The expander is configured to cooperatively engage an instrument adapted to be inserted through the trailing end of the body to engage and to move the expander from a position proximate the leading end when the body is in the collapsed position away from the leading end toward the trailing end of the body to place the body in the expanded position. The expander is adapted to contact and to move the upper, lower, and side portions away from the mid-longitudinal axis of the body. The upper, lower, and side portions of the body are adapted to cooperatively engage the expander to locate the expander at a location along the length of the body between and away from each of the leading and trailing ends and to resist dislodgment of the expander from that location when the implant is in use. The expander is adapted to hold at least a portion of the upper, lower, and side portions apart so as to maintain the expanded height and width of the body and to resist the collapse of the body to the collapsed body height and width when the body is in the expanded position.

In accordance with the purposes of a further embodiment of the present invention, as embodied and broadly described herein, an interbody spinal fusion implant is provided for implantation from at least in part an anterior approach at least in part within and across the height of a disc space between two adjacent vertebral bodies of an adult human spine. The body has a base proximate the leading end, an upper portion adapted to contact one of the adjacent vertebral bodies, a lower portion opposite the upper portion adapted to contact another one of the adjacent vertebral bodies, and at least one side portion between the upper and lower portions. Each of the upper, lower, and side portions extend from the base of the body and are spaced apart from one another to form a hollow interior therebetween. Each of the upper, lower, and side portions are configured to move at least in part in a direction away from the mid-longitudinal axis of the body to allow for expansion of the height and at least a portion of the width of the body. The upper, lower, and side portions have a collapsed position relative to one another allowing for a collapsed height and width of the body, and an expanded position relative to one another allowing for an expanded height and width of the body. The expanded height and width of the body is greater than the collapsed height and width of the body, respectively.

The implant also includes an expander at least in part within the hollow interior. The expander is configured to contact an instrument that is adapted to be inserted through the trailing end of the body to move the expander from a position proximate the trailing end when the body is in the collapsed position away from the trailing end and toward the base of the body to place the body in the expanded position. The expander is adapted to contact and to move the upper, lower, and side portions away from the mid-longitudinal axis of the body. The upper, lower, and side portions of the body are adapted to cooperatively engage the expander to locate the expander at a location along the length of the body between and away from each of the leading and trailing ends and to resist dislodgment of the expander from that location when the implant is in use. The expander is adapted to hold at least a portion of the upper, lower, and side portions apart so as to maintain the expanded height and width of the body and to resist the collapse of the body to the collapsed body height and width when the body is in the expanded position.

In accordance with the purposes of a further embodiment of the present invention, as embodied and broadly described herein, a method of this invention is provided for inserting an interbody spinal fusion implant from at least in part a posterior approach at least in part within and across the height of a disc space between two adjacent vertebral bodies of an adult human spine. The method includes providing the spinal implant having a body with a leading end for insertion first into the disc space, a trailing end opposite the leading end, a mid-longitudinal axis, upper and lower portions, and at least one side portion. Each of the upper, lower, and side portions extend from the trailing end of the body. A hollow interior is between the upper and lower portions. The implant includes an expander for expanding the height and at least a portion of the width of the body. The method includes preparing an implantation space to receive the implant from a posterior approach to the spine; inserting the implant at least in part into the implantation space; and moving the expander from a position proximate the leading end toward the trailing end of the body along at least a portion of the length of the body of the implant to move the upper, lower, and side portions in a direction away from the mid-longitudinal axis of the body of the implant to expand the height and at least a portion of the width of the body of the implant.

In accordance with the purposes of a further embodiment of the present invention, as embodied and broadly described herein, a method of this invention is provided for inserting an interbody spinal fusion implant from at least in part an anterior approach at least in part within and across the height of a disc space between two adjacent vertebral bodies of an adult human spine. The method includes providing the spinal implant having a body with a leading end for insertion first into the disc space, a trailing end opposite the leading end, a mid-longitudinal axis, upper and lower portions, and at least one side portion. Each of the upper, lower, and side portions extend from the leading end of the body. A hollow interior is between the upper and lower portions. The implant includes an expander for expanding the height and at least a portion of the width of the body. The method includes preparing an implantation space to receive the implant from an anterior approach to the spine; inserting the implant at least in part into the implantation space; and moving the expander from a position proximate the trailing end toward the leading end of the body along at least a portion of the length of the body of the implant to move the upper, lower, and side portions in a direction away from the mid-longitudinal axis of the body of the implant to expand the height and at least a portion of the width of the body of the implant.

In accordance with the purposes of a further embodiment of the present invention, as embodied and broadly described herein, an apparatus is provided for inserting at least in part within and across the height of a disc space between two adjacent vertebral bodies of the human spine a spinal implant having upper and lower portions, and an expander for expanding the height and at least a portion of the width of the implant from a collapsed position to an expanded position. The apparatus includes an inserter guide having a leading end and a trailing end. The leading end of the inserter guide is configured to cooperatively engage the trailing end of the implant. The inserter guide has a hollow interior forming a passage from the trailing end to the leading end through the inserter guide. The apparatus also includes a post adapted to be inserted at least in part through the trailing end of the implant and into a hollow interior of the implant for moving the expander along at least a portion of the length of the implant between the upper and lower portions of the implant. The post has a leading end configured to cooperatively engage the expander and a trailing end adapted to be coupled to the implant and cooperatively engage an instrument for moving the post. The apparatus also includes an inner shaft that is configured to be inserted at least in part within the passage of the inserter guide. The inner shaft has a leading end and a trailing end. The leading end of the inner shaft is configured to cooperatively engage the trailing end of the post. The inner shaft is adapted to move the post so as to move the expander toward the trailing end of the implant to expand the height and at least a portion of the width of the implant.

In accordance with the purposes of a further embodiment of the present invention, as embodied and broadly described herein, an apparatus is provided for use with a spinal implant having an expander for expanding the height of the implant from a collapsed position to an expanded position. The implant has a leading end for insertion first into a disc space between two adjacent vertebral bodies of the human spine and a trailing end opposite the leading end. The implant has at least upper and lower portions adapted to be moved away from one another by the expander when positioned therebetween. The apparatus includes an elongated shaft having a leading end and a trailing end opposite the leading end, and a mid-longitudinal axis. The apparatus also includes an enlarged head proximate the leading end of the shaft that is configured to be inserted at least in part between the upper and lower portions of the implant. The enlarged head is adapted to move apart the upper and lower portions to release the expander therebetween. The apparatus also includes a projection extending from the enlarged head that is adapted to cooperatively engage the expander for removal of the expander from within the implant.

In accordance with the purposes of a further embodiment of the present invention, as embodied and broadly described herein, an apparatus is provided for inserting at least in part within and across the height of a disc space between two adjacent vertebral bodies of the human spine a spinal implant having an expander for expanding the height and at least a portion of the width of the implant from a collapsed position to an expanded position. The implant has upper, lower, and side portions including a plurality of arms separated by spaces. The apparatus includes an inserter having a leading end and a trailing end opposite the leading end. The leading end of the inserter guide has a plurality of spaced apart portions that are configured to fit in the spaces between the arms of the spinal implant to cooperatively engage the inserter to the implant.

In accordance with the purposes of yet a further embodiment of the present invention, as embodied and broadly described herein, an apparatus is provided for holding a spinal implant having an expander for expanding the height and at least a portion of the width of the implant from a collapsed position to an expanded position. The implant has upper, lower, and side portions comprising a plurality of arms separated by spaces. The apparatus includes a sleeve having a leading end and a trailing end and a passageway from the trailing end to the leading end. The passageway provides access to the implant through the sleeve. The leading end of the sleeve has a plurality of spaced apart portions that are configured to fit in the spaces between the arms of the spinal implant to cooperatively engage the sleeve to the implant.

In accordance with the purposes of a further embodiment of the present invention, as embodied and broadly described herein, an apparatus is provided for use with a spinal implant having an expander for expanding the height of the implant from a collapsed position to an expanded position. The implant has a leading end for insertion first into a disc space between two adjacent vertebral bodies of the human spine and a trailing end opposite the leading end. The implant has at least upper and lower portions adapted to be moved away from one another by the expander when positioned therebetween. The apparatus includes an elongated shaft having a mid-longitudinal axis, a leading end, and a trailing end opposite the leading end. The leading end has a bore therein and an enlarged head with a collar in movable relationship to the head that permits rotational movement of the head independent of the collar. The collar and the head are configured to be inserted at least in part between the upper and lower portions of the implant. The collar is adapted to bear against and move apart the upper and lower portions of the implant to release the expander therebetween. The apparatus also includes a post that is adapted to be inserted at least in part through the trailing end of the spinal implant for guiding the elongated shaft along the mid-longitudinal axis between the upper and lower portions of the implant. The post has a leading end configured to cooperatively engage the implant and a trailing end that is adapted to be received within the bore of the elongated shaft. The head of the elongated shafted is adapted to rotate about the post.

It is to be understood that both the foregoing general description and the following detailed description are exemplary and explanatory only and are not restrictive of the invention, as claimed.

The accompanying drawings, which are incorporated in and constitute a part of this specification, illustrate the embodiments of the invention and together with the description, serve to explain the principles of the invention.

BRIEF DESCRIPTION OF THE DRAWINGS

FIG. 2 is an assembled trailing end perspective view of the embodiment of FIG. 1;

FIG. 3 is a trailing end elevation view of the embodiment of FIG. 2;

FIG. 4 is a side elevation view of the embodiment of FIG. 2;

FIG. 5 is a leading end elevation view of the embodiment of FIG. 2;

FIG. 6 is a leading end elevation view of a radial expander of the implant of FIG. 1;

FIG. 7 is a side elevation view of the radial expander of FIG. 6;

FIG. 8A is a trailing end elevation view of the radial expander of FIG. 6;

FIG. 8B is a trailing end elevation view of a radial expander incorporating two alternative embodiments in accordance with the present invention;

FIG. 9 is a partial side sectional view of the embodiment of FIG. 2 prior to the implant being radially expanded;

FIG. 10 is a partial side sectional view of the embodiment of FIG. 2 with the implant in partial radial expansion;

FIG. 11 is a partial side sectional view of the embodiment of FIG. 2 with the implant in a radially expanded state;

FIG. 12 is a side elevation view of one embodiment of a driver instrument for inserting the implant of FIG. 1;

FIG. 13 is a distal end view of the driver instrument of FIG. 12;

FIG. 14 is a perspective proximal end view of the funnel-shaped end of the driver instrument of FIG. 12;

FIG. 15 is a side elevation view of one embodiment of a rotating instrument used to rotate the threaded post to move the radial expander to radially expand the implant of FIG. 1;

FIG. 16 is a side elevation view of one embodiment of a plunger instrument for inserting bone growth promoting material into the implant of FIG. 1 and the disc space;

FIG. 17 is a side elevation view of the plunger instrument of FIG. 16 in an extended state;

FIG. 19 is a side view of the guard of FIG. 18 being inserted within the spine with the disc penetrating extensions parallel to one another in the insertion position;

FIG. 20 is a side view of the guard of FIG. 18 in the deployed position with the disc penetrating extensions shown in an expanded position to induce angulation of the adjacent vertebral bodies;

FIG. 26 is a partial side sectional view of the guard and driver instrument with the plunger instrument of FIG. 16 inserted therein and being used to fill the interior of the implant of FIG. 1 with bone growth promoting material;

FIG. 27 is a partial side sectional view of the guard and driver instrument with the instrument of FIG. 16 in an extended state inserted therein for delivering bone growth promoting material beyond the radial expander and to regions of the disc space beyond the leading end of the implant not occupied by the implant;

FIG. 34 is a side elevation view of the embodiment of FIG. 33;

FIG. 35 is a leading end elevation view of the embodiment of FIG. 33;

FIG. 36 is a trailing end elevation view of the embodiment of FIG. 33;

FIG. 37 is a perspective view of an alternative embodiment of the implant and threaded post of FIG. 33 having two diametrically opposed shortened arms;

FIG. 38 is a perspective view of an alternative embodiment of the implant of FIG. 33 having arms of generally the same length;

FIG. 42 is a fragmentary side elevation view of the leading end of one embodiment of a driver instrument for inserting the implant of FIG. 33;

FIG. 43 is a side elevation view of one embodiment of an instrument for holding the implant of FIG. 33 while the radial expander of FIG. 33 is advanced through the interior of the implant;

FIG. 44 is a fragmentary side elevation view in partial cross section of one embodiment of a rotating instrument used to linearly advance the radial expander along the threaded post and into the implant to radially expand the implant of FIG. 33;

FIG. 45 is a fragmentary side elevation view in partial cross section of one embodiment of an instrument for use in removing the post from the implant of FIG. 33;

FIG. 54 is a side elevation view of a preferred embodiment of a remover instrument used to remove an installed radial expander from an implant to collapse the implant of FIG. 33 into a non-expanded state;

DETAILED DESCRIPTION OF THE DRAWINGS

Figure 1:
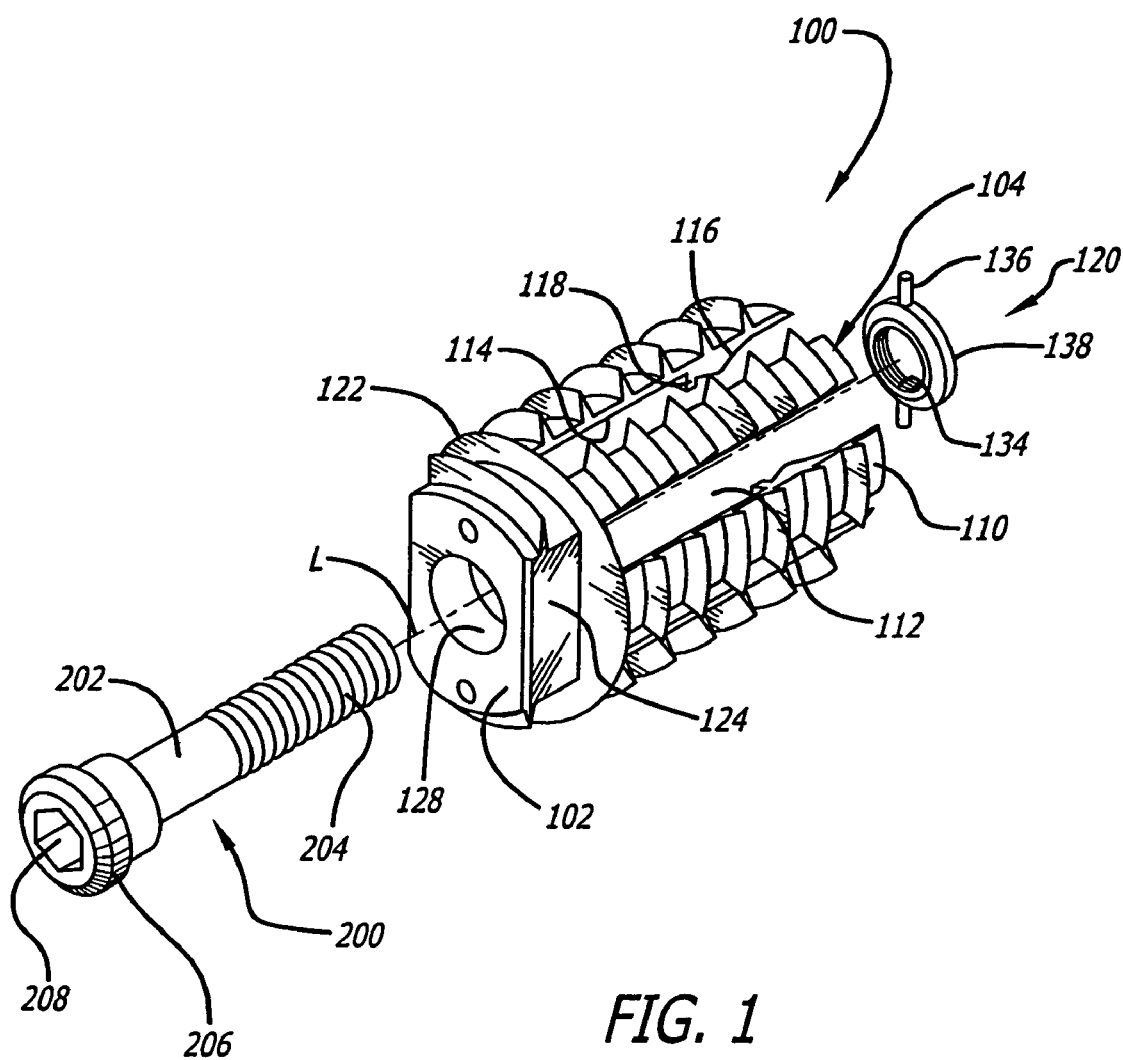
FIG. 1 is an exploded perspective view of a spinal fusion implant, radial expander of the implant, and threaded post in accordance with a preferred embodiment of the present invention for posterior insertion into the spine.

The following description is intended to be representative only and not limiting and many variations can be anticipated according to these teachings, which are included within the scope of this inventive teaching. Reference will now be made in detail to the preferred embodiments of this invention, examples of which are illustrated in the accompanying drawings.

FIGS. 1-11 show a preferred embodiment of a radially expandable implant and threaded post used to expand the implant in accordance with the present invention. As shown in FIGS. 1-5, implant 100 preferably is a spinal fusion implant adapted to be installed from at least in part a posterior approach to the spine into an implantation space formed across the height of a spinal disc and into two adjacent vertebral bodies. Implant 100 has a body with a trailing end 102, a leading end 104 for insertion first into the disc space, and preferably has a hollow interior 103. Leading end 104 is preferably open to permit access to hollow interior 103 of implant 100 through leading end 104. Hollow interior 103 is preferably configured to hold at least some bone growth promoting material therein.

Implant 100 includes at least upper and lower arcuate portions 106a and 106b adapted to be oriented toward and contact adjacent upper and lower vertebral bodies, respectively, and preferably has opposite sides 108a and 108b. Arcuate portions 106a, 106b and sides 108a, 108b include arms 110 that extend from trailing end 102 along at least a part of the length of the implant toward leading end 104. Arms 110 are preferably separated by a space 112. Spaces 112 may be of different lengths and widths and may, for example, be in the shape of a slit, a slot, or any other shape suitable for the intended purpose of spacing apart arms 110. Preferably, spaces 112 permit for the growth of bone from adjacent vertebral body to adjacent vertebral body through the body of implant 100.

As best shown in FIGS. 9-11, arms 110 have an interior surface 114 facing hollow interior 103 of implant 100 configured to bear against and hold a radial expander for forcing apart arms 110 from within hollow interior 103. Preferably, upper portion 106a, lower portion 106b, and at least one of sides 108a, 108b are configured to locate an expander along the length of the body of implant 100 between and away from each of trailing and leading ends 102, 104 and to resist dislodgement of the expander when implant 100 is in use. Interior surface 114 of arms 110 of at least upper and lower arcuate portions 106a, 106b preferably has a ramped portion 116 and seat 118 for receiving an expander 120. Each arm 110 preferably is of such length, thickness, and material to resist rotational torquing forces during rotation of implant 100 while being flexible enough to move in a radial direction away from the mid-longitudinal axis of implant 100 when forced apart from the interior of implant 100. For example, one embodiment of implant 100 has six arms 110, each of which flexes in a radial direction away from the mid-longitudinal axis; thus, each arm 110 moves in a direction different from that of any of the other arms 110 of implant 100. Preferably, each arm 110 is sufficiently resilient so that each arm 110 may be moved away from the mid-longitudinal axis of implant 100 and may be permitted to return to its original orientation if desired without substantial deformation. Examples of preferred materials for arms 110 include, but are not limited to, metals such as titanium and stainless steel, plastics, and carbon fibers among others. Arms 110 may be engineered to have a flexibility and springiness optimal for the stiffness of the area of the spine into which they are to be implanted.

In the expanded position, arms 110 may be at least in part concave along at least a portion of the length of implant 100. A concave configuration of arms 110 provides a desirable springiness and resilience for contacting and supporting the vertebral bodies adjacent implant 100. Although it is preferred to have movable arms 110 spaced around the entire circumference of the implant, the invention is not so limited. By way of example only, one or more arms 110 may be truncated or omitted from a side or sides to limit the expansion of the width of the implant. A preferred embodiment of implant 100 would have at least two arms 110 on each of upper and lower arcuate portions 106a, 106b, each of arms 110 being adapted to be radially expanded in a direction away from the mid-longitudinal axis of implant 100. To accommodate side-by-side placement of implants, arms 110 may be of different lengths. Implant 100 preferably includes at least one external thread 122 to permit for the rotational insertion of implant 100 into the disc space and between adjacent vertebral bodies a human spine. Although a preferred embodiment of the implant includes threads, the invention is not so limited. For example, the exterior of implant 100 may include other bone engaging surfaces such as projections, splines, knurling, ratchets, or other surface roughenings to resist expulsion of the implant from the implantation space after implantation.

As shown in FIGS. 1-4, trailing end 102 preferably is configured to cooperatively engage a driver 300 shown in FIG. 12 used to install implant 100 into the disc space. For example, trailing end 102 may include truncated sides 124 for cooperatively engaging flanges 310 of driver 300 and recesses 126a and 126b for engaging pins 312a and 312b, respectively, of driver 300. Trailing end 102 of implant 100 has an opening 128 sized for receiving a post 200 for engagement with radial expander 120.

Post 200 is configured to be inserted into implant 100 through trailing end 102. Post 200 preferably has a shaft 202 with at least one thread 204 and a head 206. Head 206 includes a tool engagement area 208 for cooperatively engaging a tool used for inserting and removing post 200 from implant 100. Area 208 is shown as having a hex-shaped engagement surface, but it is understood that area 208 may have any configuration suitable for its intended purpose. The distal end of post 200 passes through opening 128 of implant 100 and extends into the interior of implant 100 to engage radial expander 120. Thread 204 is adapted to cooperatively engage radial expander 120 to move radial expander toward trailing end 102 of implant 100 and force arms 110 apart to expand implant 100. Shaft 202 may be at least in part smooth to permit movement of shaft 202 within opening 128 without engagement to opening 128.

As shown in FIGS. 6-8A, radial expander 120 is configured to be inserted at least in part within hollow interior 103 of implant 100. Expander 120 preferably has a leading face 130 adapted to be oriented toward trailing end 102 of implant 100 and an opposite trailing face 132 adapted to be oriented toward leading end 104 of implant 100 when inserted within hollow interior 103 of implant 100. A preferred radial expander 120 has an opening 134, guide pegs 136, and a rim 138 adapted to bear against interior surface 114 of arms 110. Radial expander 120 is preferably at least in part circular or may have any other configuration suitable for its intended purpose. Opening 134 is preferably threaded to cooperate with thread 204 of post 200 to move radial expander 120 toward trailing end 102 of implant 100. Although threaded rotational engagement is preferred for moving radial expander 120, the invention is not so limited. For example, post 200 may be configured to engage radial expander 120 with a retractable flange or projection and pull expander 120 into position to expand arms 110. Preferably, expander 120 has a fixed shape.

Guide pegs 136 of radial expander 120 are adapted to fit within spaces 112 such that as post 200 is rotated, radial expander 120 advances in a linear direction away from leading end 104 towards trailing end 102 of implant 100. Pegs 136 prevent substantial rotation of radial expander 120 during rotation of post 200. Although two guide pegs 136 are shown extending from radial expander 120, the number and shape of pegs 136 may be varied as suitable for their intended purpose.

FIG. 8B shows a radial expander 120' incorporating two alternative embodiments in accordance with the present invention. Radial expander 120' is adapted to selectively expand the height of implant 100 and to limit or prevent the expansion of the width of implant 100. The configuration of radial expander 120' provides for the selective movement of one or more arms 110 away from the mid-longitudinal axis of implant 100 as radial expander 120' is advanced into implant 100. For example, radial expander 120' may have one or more truncated sides 135 to form a reduced width portion of radial expander 120'. Truncated side 135 is preferably configured to avoid contact with the interior surface 114 of arms 110 adjacent truncated side 135 and is preferably configured to clear interior surface projections such as, for example, ramp 116 of arm 110 during the advancement of radial expander 120' toward leading end 102. Instead of truncated side 135, radial expander 120' may include a groove 137 configured to receive at least a portion of an arm 110 adjacent thereto. In its preferred use, at least the upper and lower portions of rim 138 of radial expander 120' bear against the interior surface 114 of arms 110 to expand the height of implant 100 so as not to induce expansion of any arm or arms 110 adjacent truncated side 135 or groove 137, as the case may be. The expansion of the implant may be controlled by the interaction of the radial expander and arms of the implant to expand the width to only one side or to expand both sides by different amounts and involve one or more arms on a side of the implant. It is appreciated that other configurations of radial expander 120' are possible to achieve its intended purpose without departing from the scope of the present invention.

FIG. 9 shows implant 100 in a collapsed state. After insertion into the disc space, post 200 is rotated, causing radial expander 120 to travel within the interior of implant 100 from a position proximate leading end 104 toward trailing end 102. Pegs 136 travel within space 112 and can contact the sides of arms 110 to limit rotation of radial expander 120 during rotation of post 200.

FIG. 10 shows rim 138 of radial expander 120 moved along interior surface 114 of implant 100 after post 200 is initially rotated, and shows rim 138 in contact with ramp portions 116 of implant 100. Movement of radial expander 120 away from leading end 104 along ramp portions 116 forces arms 110 to move away from the mid-longitudinal axis of implant 100 and toward the adjacent vertebral bodies.

As shown in FIG. 11, continued rotation of post 200 causes radial expander 120 to traverse ramp portions 116 and enter seat 118 of implant 100. The entrance to seat 118 is narrower than the remainder of seat 118 to prevent radial expander 120 from backing-out. Radial expander 120 is further held into place within seat 118 by arms 110. The sloped sides of seat 118 form an inclined plane that inhibits movement of radial expander 120 toward leading end 104 of implant 100. With radial expander 120 seated in seat 118, arms 110 are forced apart at a greater distance as measured from leading end 104 to the mid-longitudinal axis than from trailing end 102 to the mid-longitudinal axis to place implant 100 into an expanded state. After implant 100 is in the expanded state, post 200 can be removed from implant 100 by rotation in the opposite direction, and radial expander 120 remains in seat 118 to maintain the expanded height and width of implant 100.

FIGS. 12-14 show an implant driver 300 for inserting implant 100 into a disc space. Implant driver 300 has a shaft 302, a distal end 304, and a proximal end 306. Shaft 302 is preferably hollow and is adapted to permit the passage of other instruments therethrough as described below. Distal end 304 includes an implant engaging head 308 with flanges 310, pins 312a, 312b, and an opening 314. Implant engaging head 308 is sized and shaped to cooperatively engage an implant to hold and manipulate the implant during insertion into the disc space. Proximal end 306 includes a handle 316 for rotational and linear advancement of driver 300. Proximal end 306 preferably has a funnel-shaped opening 318 passing through shaft 302 and expanding through distal end 304. Funnel-shaped opening 318 is preferably configured as shown in FIG. 14 to facilitate the introduction of bone growth promoting material into shaft 302. Funnel-shaped opening 318 is preferably sized and shaped to receive other instruments therethrough, such as plunger 500 described in association with FIGS. 16 and 17 below.

FIG. 15 shows a rotating tool 400 for engaging and rotating post 200. Rotating tool 400 has a distal end 402 and a proximal end 404. Distal end 402 has a tip 406 adapted to cooperatively engage area 208 of post 200. In a preferred embodiment, tip 406 is hex-shaped, but may be of any shape suitable to engage post 200. Tip 406 is preferably adapted to engage area 208 of post 200 such that upon the disengagement of post 200 from implant 100, rotating tool 400 can withdraw post 200 through shaft 302 of driver 300. In order to facilitate the removal of post 200 such that post 200 and rotating tool 400 may be removed together, tip 406 may be adapted to cooperatively engage with area 208, for example, via an interference fit, detent, or retractable spring flange. Proximal end 404 is preferably configured to engage a handle and has a stop 408. Proximal end 404 is preferably adapted to engage with a mechanical or manual device for rotating shaft 410.

FIGS. 16 and 17 show a plunger instrument for inserting bone growth promoting material into implant 100 and into the surrounding disc space. Plunger 500 preferably has an outer shaft 502, an inner rod 504, and a handle 506. Inner rod 504 preferably has a proximal end configured to engage a handle, such as a T-handle for example, and a stop 508 for limiting the travel of inner rod 504 when placed within outer shaft 502. In use, plunger 500 may be inserted into an instrument adapted to deliver bone growth promoting material into implant 100 such as driver 300. Plunger 500 and driver 300 together may be placed within a guard such as guard 600 of FIG. 18 to introduce bone growth promoting material into hollow interior 103 of implant 100 and preferably the disc space surrounding the implant.

In a preferred embodiment, bone growth promoting material is introduced into hollow interior 103 of shaft 302 of driver 300 through funnel-shaped opening 318. Plunger 500 with inner rod 504 inserted therein, may be inserted into the interior of driver 300 to push bone growth promoting material therethrough and into the implant. Plunger 500 and inner rod 504 may further move bone growth promoting material into the remaining areas inside and around the implant not yet filled with bone growth promoting material.

Plunger 500 preferably has a clamp 510 and stop 508 to limit the extension of inner rod 504 from outer shaft 502. Stop 508 may have any configuration adapted to limit the travel of inner rod 504, for example, a shoulder, flange, or other projection. Although it is preferred that inner rod 504 is solid, the invention is not so limited. Clamp 510 in the tightened position holds inner rod 504 in fixed relationship to outer shaft 502 and preferably so as not to extend from the distal end of shaft 502. When clamp 510 is released, inner rod 504 is permitted to travel beyond the distal end of outer shaft 502 to the extent limited by stop 508.

FIGS. 18-30 show various steps of a preferred method for inserting implant 100 and using associated instrumentation disclosed herein.

Figure 18:
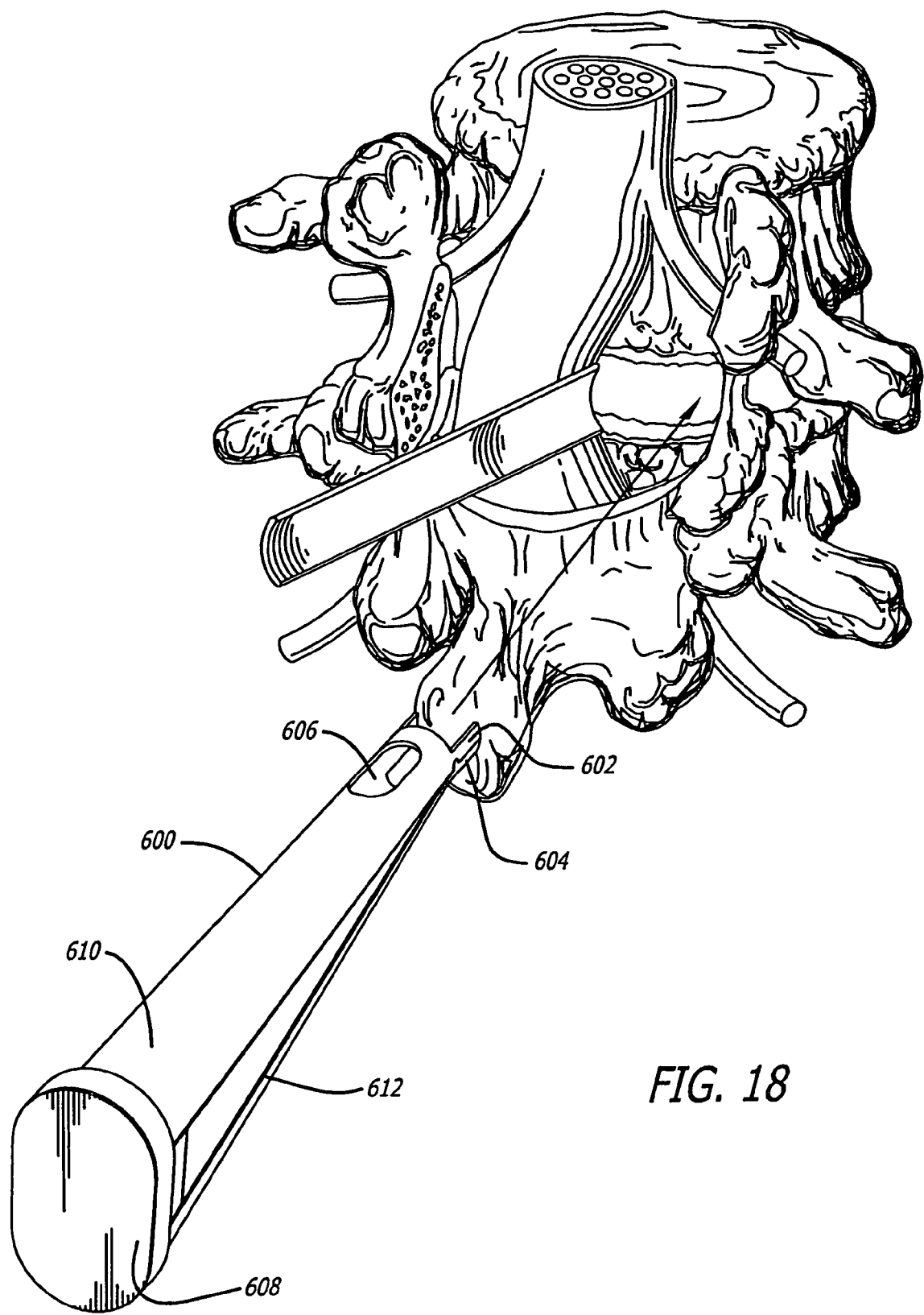
FIG. 18 is a perspective view of the posterior aspect of a lumbar segment of a spine with the dural sac retracted to the left showing a partial discectomy and an expandable guard with disc penetrating extensions approaching the disc space between the adjacent vertebral bodies with the disc penetrating extensions in an insertion position.

FIG. 18 is a perspective view of a segment of a spine viewed from a posterior aspect with the dural sac retracted to the left showing that a partial discectomy has already been performed. Guard 600, with disc penetrating extensions 602, 604 and window 606, is shown approaching the disc space between the adjacent vertebral bodies with disc penetrating extensions 602, 604 in a first or insertion position.

It is appreciated that various types of guards may be used to provide protected access to the disc space including, but not limited to, those taught by Michelson in application Ser. Nos. 10/085,731 and 10/085,406; and U.S. Pat. Nos. 5,015,247; 5,484,437; 6,080,155; and 6,210,412 all of which are incorporated herein by reference.

An impaction cap 608 is positioned on the proximal end of guard 600 to maintain it in the open position such that the disc penetrating extensions are closed into the insertion position. In this position, guard 600 is ready to be placed or driven into the disc space between the adjacent vertebral bodies.

In FIG. 19, the extensions of guard 600 are fully inserted into the spine with the disc penetrating extensions parallel to one another in the insertion position. Impaction cap 608 is shown holding the guard in the open position and the disc penetrating extension in the insertion position. Guard 600 rotationally articulates to permit movement of disc penetrating extensions 602, 604 in response to movement of a first portion 610 and a second portion 612 relative to one another. The rotational articulation preferably occurs about a hinge 614, which is preferably formed in first and second portions 610, 612.

In FIG. 20, guard 600 is shown in a closed position with the disc penetrating extensions shown in the inserted position to induce lordosis to the vertebral bodies. After closing guard 600, the proximal end has a lock collar 616 placed around it to maintain guard 600 in the closed position.

Figure 21:
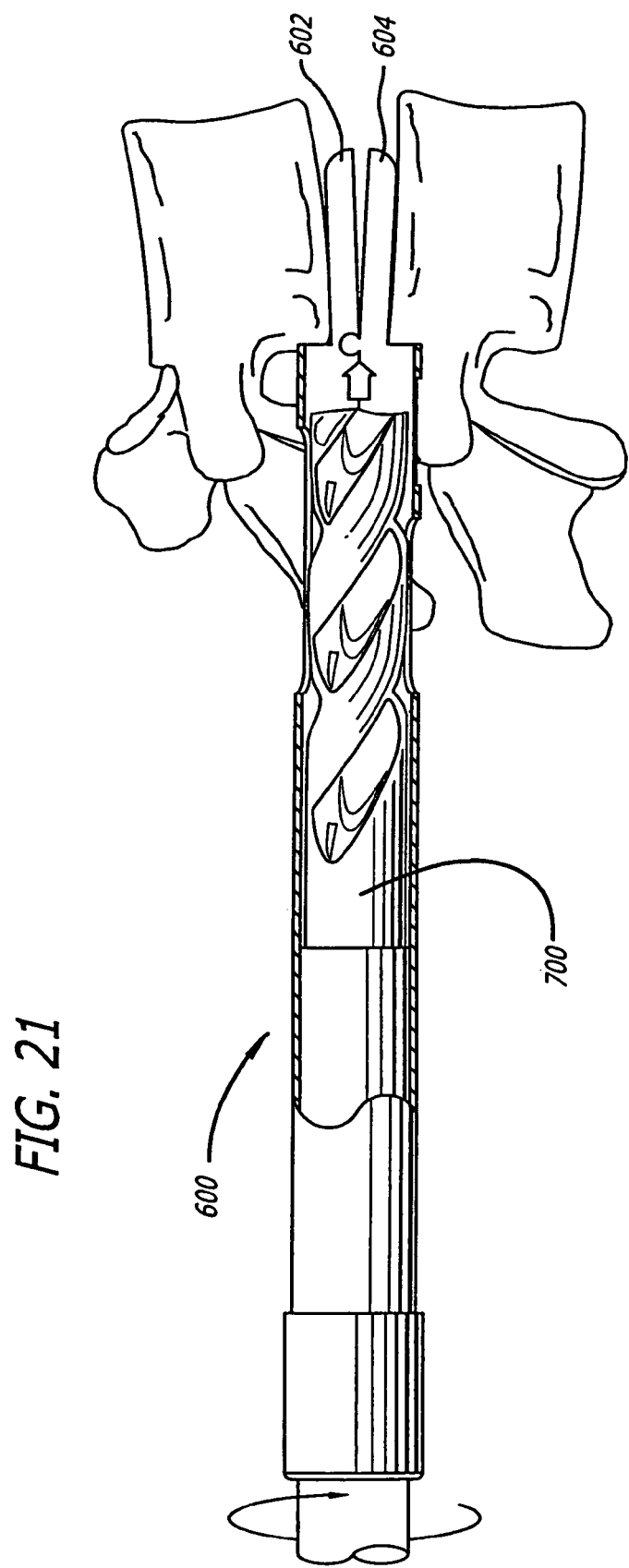
FIG. 21 is a side view of the guard of FIG. 18 in the deployed position with the disc penetrating extensions in an expanded position to induce angulation of the adjacent vertebral bodies and in partial cross-section to show a side view of a drill being inserted through the guard.

In FIG. 21, guard 600 is in a closed position with disc penetrating extensions 602, 604 in the inserted position to induce angulation to the adjacent vertebral bodies. At the distal end of guard 600 shown in cross-section is a side view of a bone removal device such as a drill 700 being inserted through guard 600. It is appreciated that other bone removal devices suitable for the intended purpose such as, but not limited to, burrs, reamers, mills, saws, trephines, chisels, and the like may also be used and would be within the scope of the present invention. Guard 600 provides protected access to the disc space and the adjacent vertebral bodies for drill 700 via the elongated opening in guard 600.

Drill 700 may have a reduced diameter-cutting portion relative to the shaft diameter of guard 600 or may be inserted through an inner sleeve that passes into guard 600 to guide drill 700 to form an implantation space smaller than the passage through guard 600. Thus, the guard opening may be taller than the height of the cutting portion of drill 700. Such a taller opening also allows the implantation of an implant taller than the height of the cutting portion of drill 700.

Figure 22:
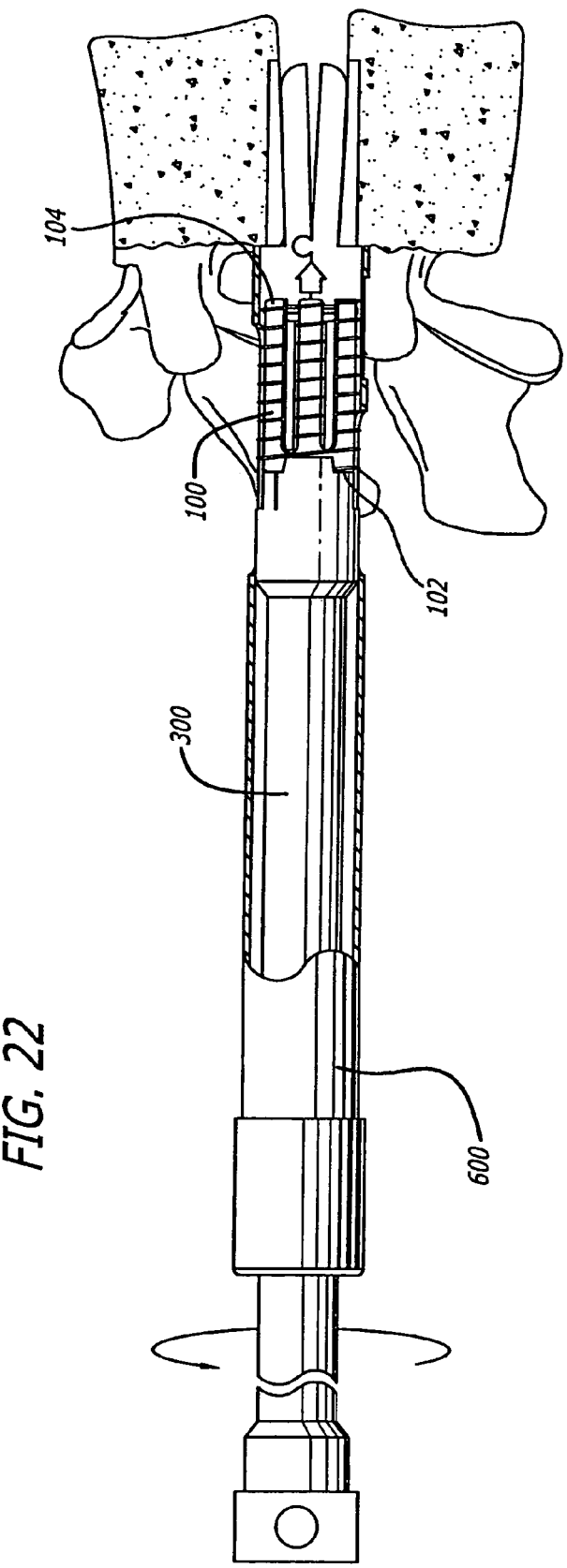
FIG. 22 is a side view of the guard of FIG. 18 in partial cross-section showing the spinal fusion implant of FIG. 1 and the driver instrument of FIG. 12 passing through the guard to install the implant into a prepared implantation space across the height of the restored disc space and into the adjacent vertebral bodies.

As best shown in FIG. 22, implant 100 and implant driver 300 may be passed through guard 600 to insert implant 100 in a collapsed position into the disc space between the adjacent vertebral bodies. The guard may be left in place throughout the procedure. Implant 100 is assembled with post 200 inserted through trailing end 102 of implant 100 to engage radial expander 120 inserted in the collapsed position into hollow interior 103 of implant 100 through leading end 104. Radial expander 120 in this position may bear against the interior surface 114 of arms 110 but does not yet force arms 110 apart so that implant 100 is in a non-expanded state. Implant 100 is preferably rotated into the disc space such that thread 122 penetrably engages the bone of the adjacent vertebral bodies.

Figure 23:
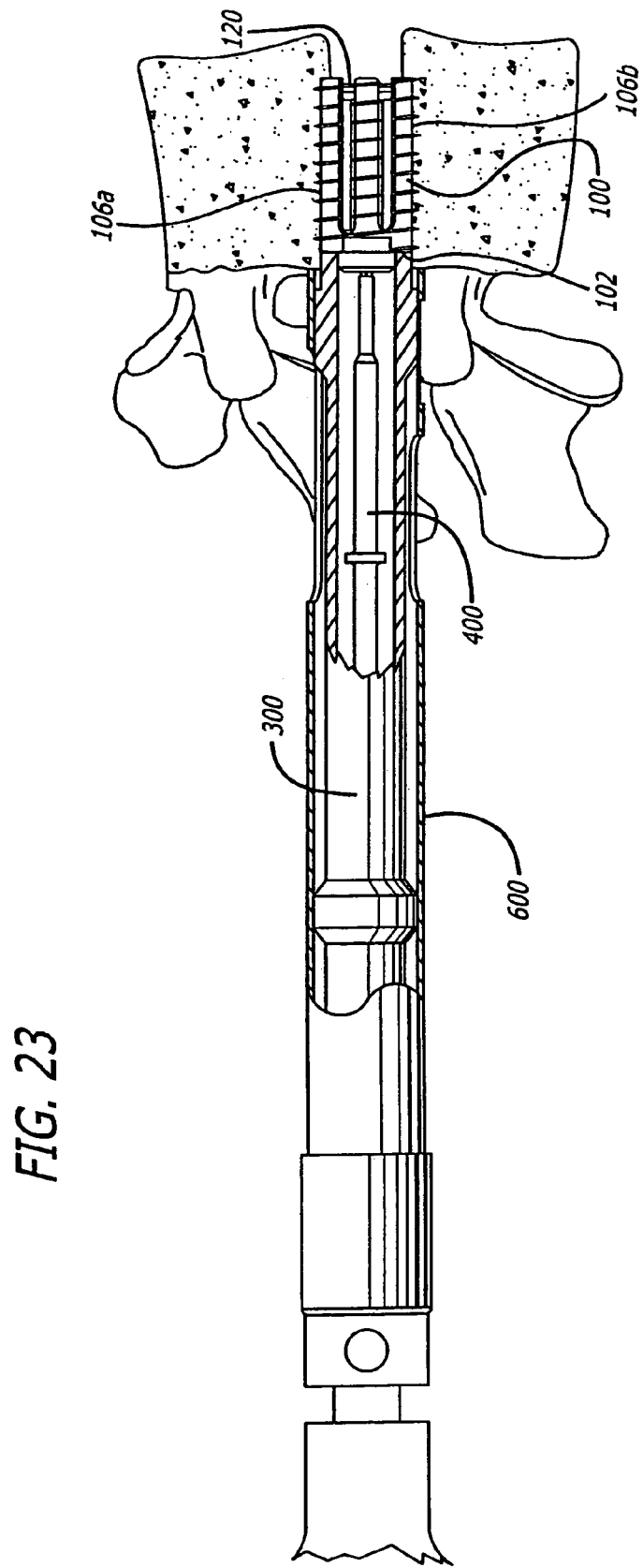
FIG. 23 is a side view of the implant of FIG. 1 in a non-expanded state inserted into the implantation space and the rotating instrument of FIG. 15 passing through the driver instrument of FIG. 12 and guard of FIG. 18 both shown in partial cross section to engage the threaded post.

As illustrated in FIG. 23, after implant 100 is installed in the desired position in the implantation space between the adjacent vertebral bodies with opposed arcuate portions 106a and 106b oriented toward the adjacent vertebral bodies, rotating tool 400 is used to engage and rotate post 200 so as to pull radial expander 120 away from leading end 104 and toward trailing end 102 along the interior surface 114 of arms 110 to transition implant 100 from a collapsed position to an expanded position.

Figure 24:
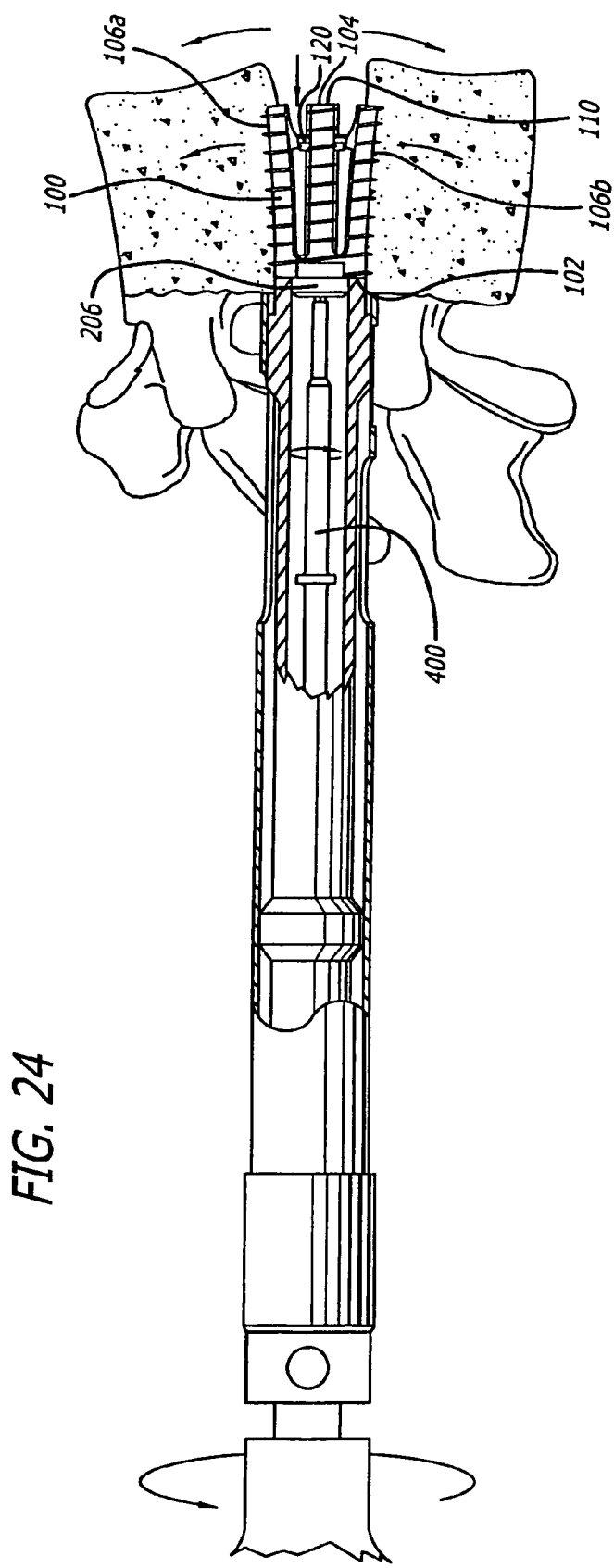
FIG. 24 is a side view of the implant of FIG. 1 radially expanded in the implantation space via the rotating instrument of FIG. 15 that passes through the driver instrument and guard both shown in partial cross section.

As shown in FIG. 24, as rotating tool 400 is rotated, radial expander 120 moves toward trailing end 102 of implant 100 causing arms 110 to move radially outward away from the mid-longitudinal axis of implant 100. The interaction between radial expander 120 and arms 110 is best shown in FIGS. 9-11. The radial expansion of implant 100 results in a greater implant height and width proximate leading end 104 than the implant height and width proximate trailing end 102. Upper and lower arcuate portions 106a, 106b are positioned in angular relationship to each other and position the vertebral bodies adjacent implant 100 in an angular relationship to each other.

Figures 25, 25A:
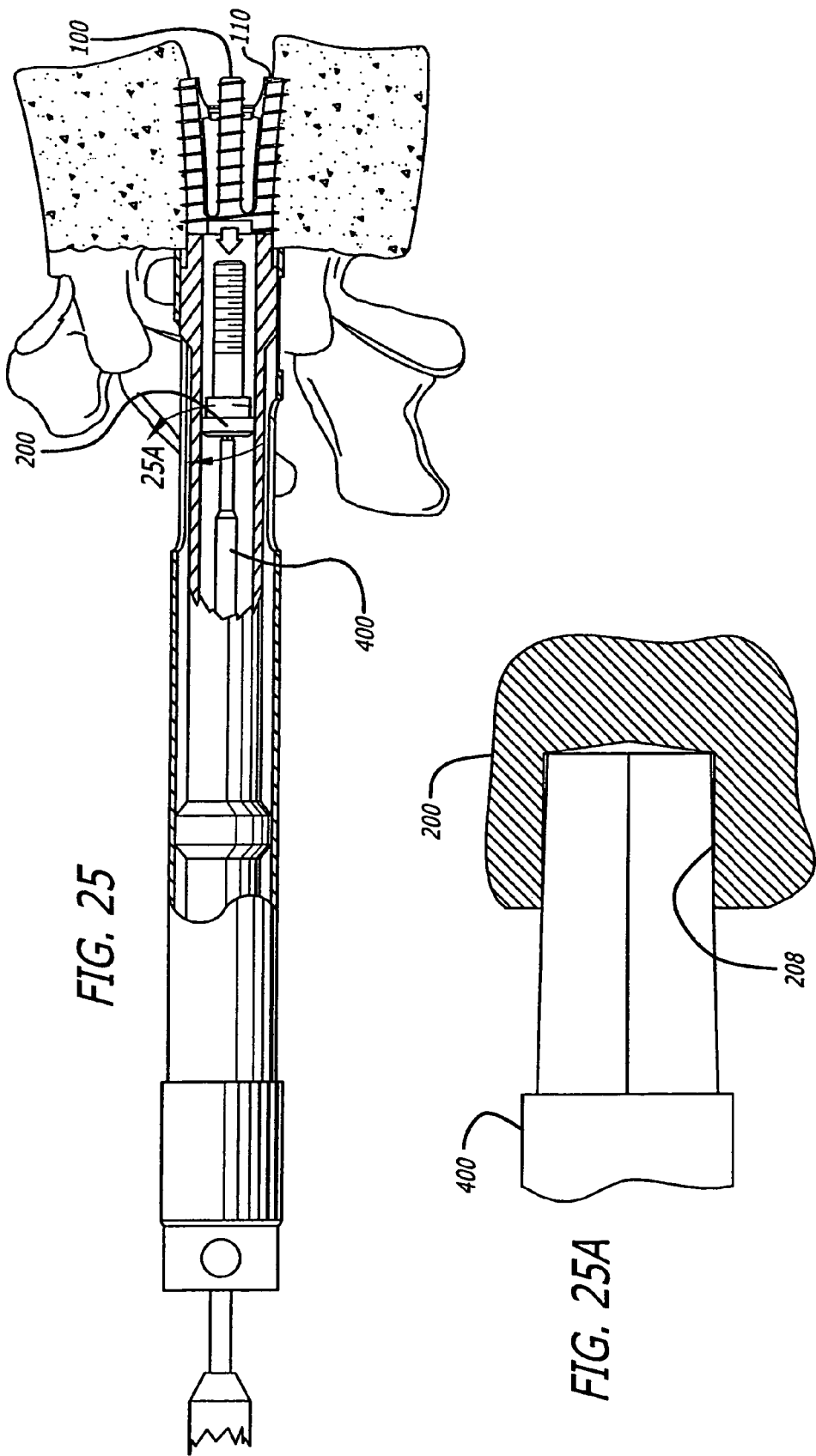
FIG. 25 is a side view of the rotating instrument of FIG. 15 removing the threaded post from the implant of FIG. 1 through the driver instrument and guard both shown in partial cross section.
FIG. 25A is an enlarged fragmentary view along line 25A of FIG. 25 showing the cooperative engagement of the driver instrument and threaded post.

As shown in FIGS. 25 and 25A, after implant 100 is in the expanded state, post 200 is removed by rotating tool 400 from implant 100. Rotating tool 400 is adapted to cooperatively engage tool engagement area 208 of post 200. The leading end of rotating tool 400 may be tapered to allow the tip of tool 400 to slightly bind and positively engage tool engagement area 208. Radial expander 120 remains seated within hollow interior 103 of implant 100 to hold arms 110 in a radially expanded state.

FIGS. 26 and 27 show a preferred method for insertion of bone growth promoting materials into implant 100 and the disc space surrounding implant 100. Driver 300 is shown inserted into guard 600 with its distal end adjacent to and in communication with opening 128 of implant 100 to access hollow interior 103 of implant 100. Bone growth material is introduced into funnel shaped end 318 of driver 300. Plunger 500 with inner rod 504 in the retracted position is used to push and load the bone growth promoting material through shaft 302 of driver 300 and into implant 100. Sufficient bone growth material is introduced into driver 300 to at least partially fill implant 100. Alternatively, the implant may be pre-loaded with bone growth promoting material prior to its insertion into the implantation space. Additional bone growth material may be added to fill any space within the implant created as a result of transitioning implant 100 to an expanded position as described below.

As shown in FIG. 27, after the implant is at least partially filled with bone growth promoting material, inner rod 504 is moved forward in the extended position into implant 100 through opening 128 of trailing end 102 to push the bone growth promoting material in its path through opening 134 of radial expander 120. Distributing bone growth promoting material beyond radial expander 120 fills the interior of implant 100 proximate leading end 104 and introduces bone growth promoting material further into the disc space beyond leading end 104 and unoccupied by implant 100. After inner rod 504 is retracted from within the interior of implant 100 and plunger 500 is removed from driver 300, additional bone growth promoting material may be inserted into driver 300. Plunger 500 then may be used to fill the space left unoccupied by the removal of inner rod 504 with bone growth promoting material and further pack bone growth promoting material into implant 100. After filling implant 100 and the surrounding disc space with bone growth promoting material, plunger 500 and driver 300 are removed from guard 600. The trailing end of guard 600 is then opened to return disc penetrating extensions 602, 604 to the closed position to facilitate the removal of guard 600 from the disc space.

Figure 28:
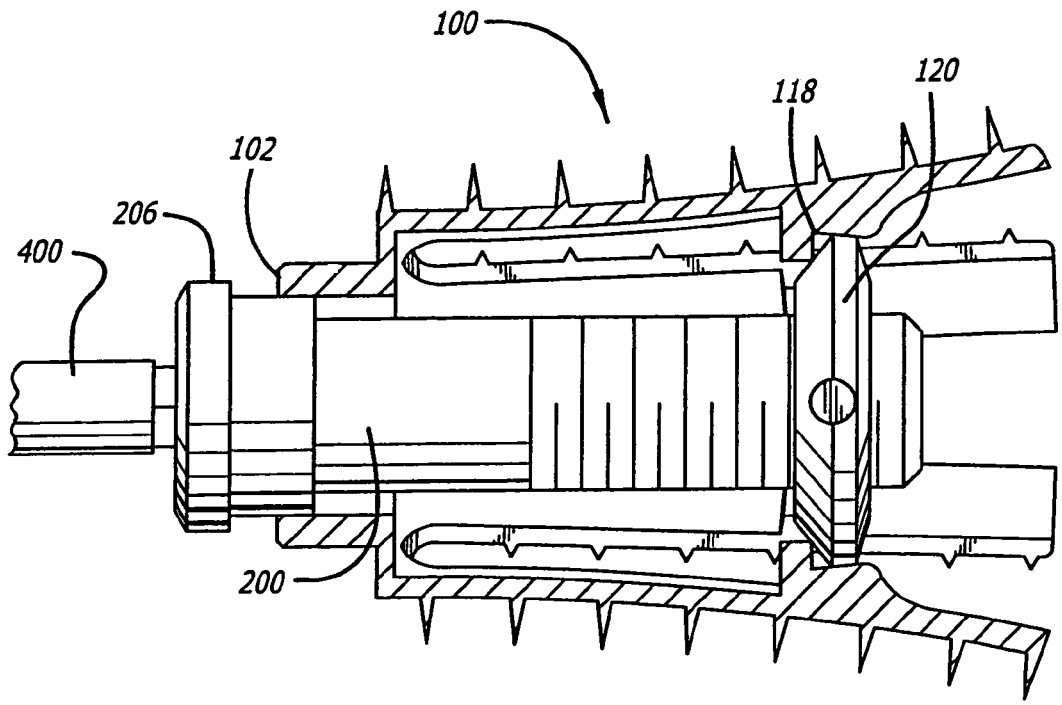
FIG. 28 is a partial side sectional view of the implant of FIG. 1 in an expanded state with the threaded post being partially threaded into the radial expander.
Figure 29:
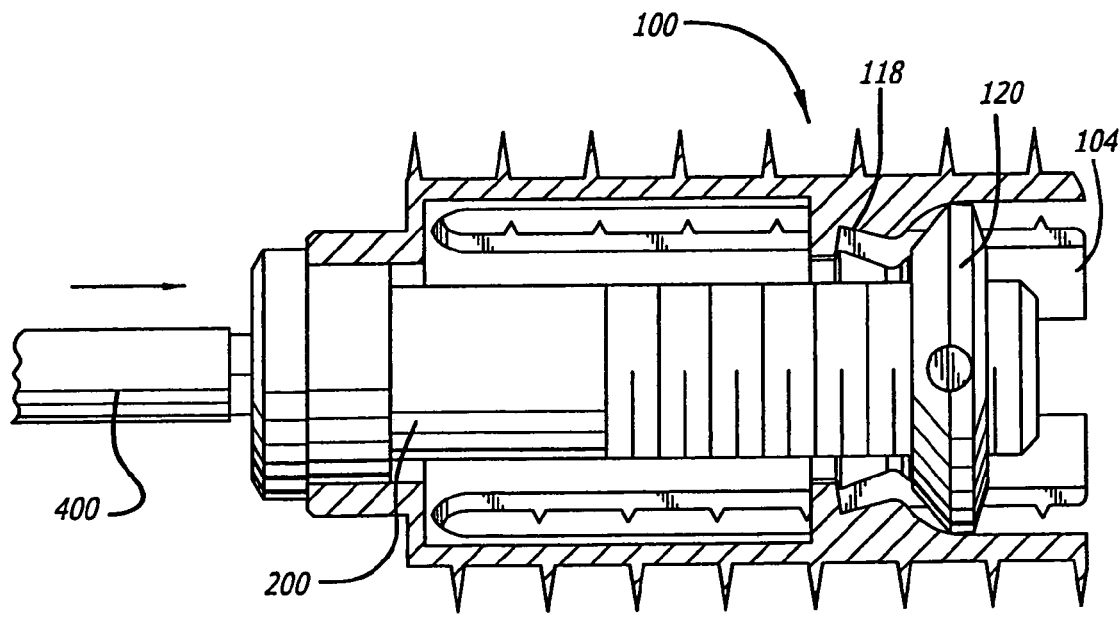
FIG. 29 is a partial side sectional view of the implant of FIG. 1 with the post partially threaded into the radial expander being advanced toward the leading end of the implant to unseat the radial expander and return the implant to the non-expanded state for posterior extraction of the implant from the implantation space.

FIGS. 28-32 show a preferred remover and methods of disengaging radial expander 120 from seat 118 of implant 100 if it is desired to uninstall implant 100 or other implants of the present invention designed for a generally posterior insertion. FIG. 28 shows post 200 being partially threaded into a seated radial expander 120 by rotating tool 400 such that a portion of post 200 extends from trailing end 102 of implant 100. As shown in FIG. 29, post 200 may then be advanced in a linear direction without substantial rotation toward leading end 104 of implant 100 such as, for example, with an impaction force. The linear advancement of post 200 toward leading end 104 moves expander 120 out of seat 118 and toward leading end 104. This allows the implant arms to collapse inward to the unexpanded state, thereafter allowing the implant to be unthreaded or otherwise removed from the spine. The implant holder may be attached prior to collapsing the implant or thereafter. With expander 120 removed from the interior of implant 100, arms 110 are no longer held in a radially expanded position, thereby causing implant 100 to collapse to an unexpanded state.

Figure 30:
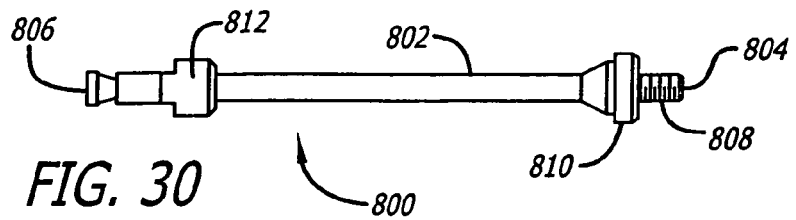
FIG. 30 is a side elevation view of one embodiment of a remover instrument used to unlock and remove a seated radial expander from an anterior approach and through the leading end of the implant to place the implant of FIG. 1 into a non-expanded state.
Figure 31:
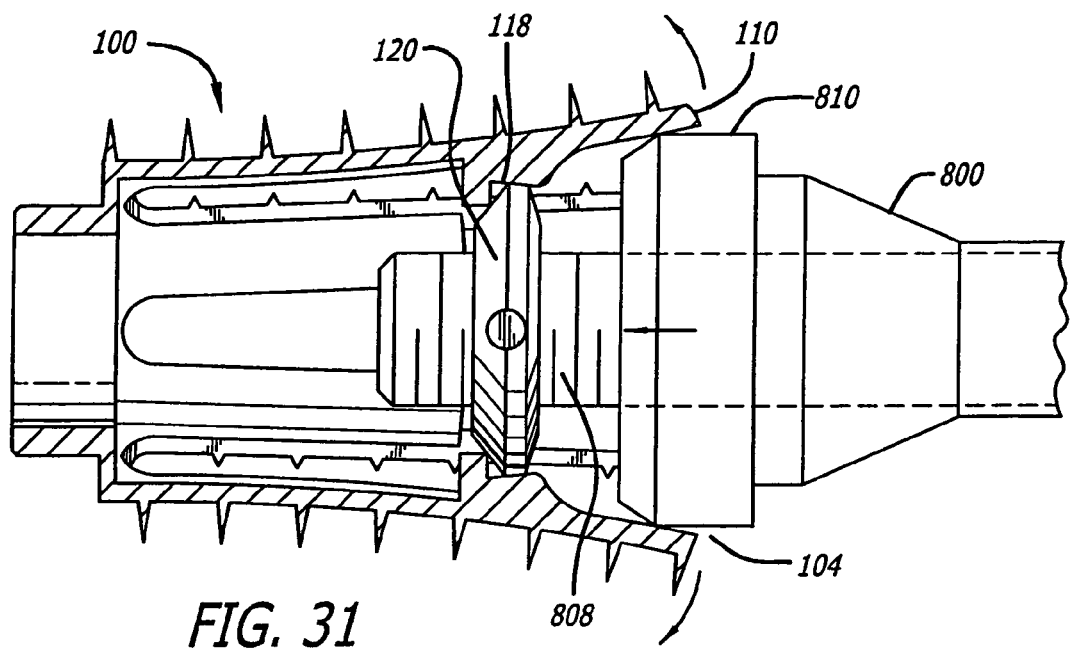
FIG. 31 is a partial side sectional view of the remover instrument of FIG. 30 being used to expand the implant anteriorly to unlock and displace the expander to allow for removal of the implant.
Figure 32:
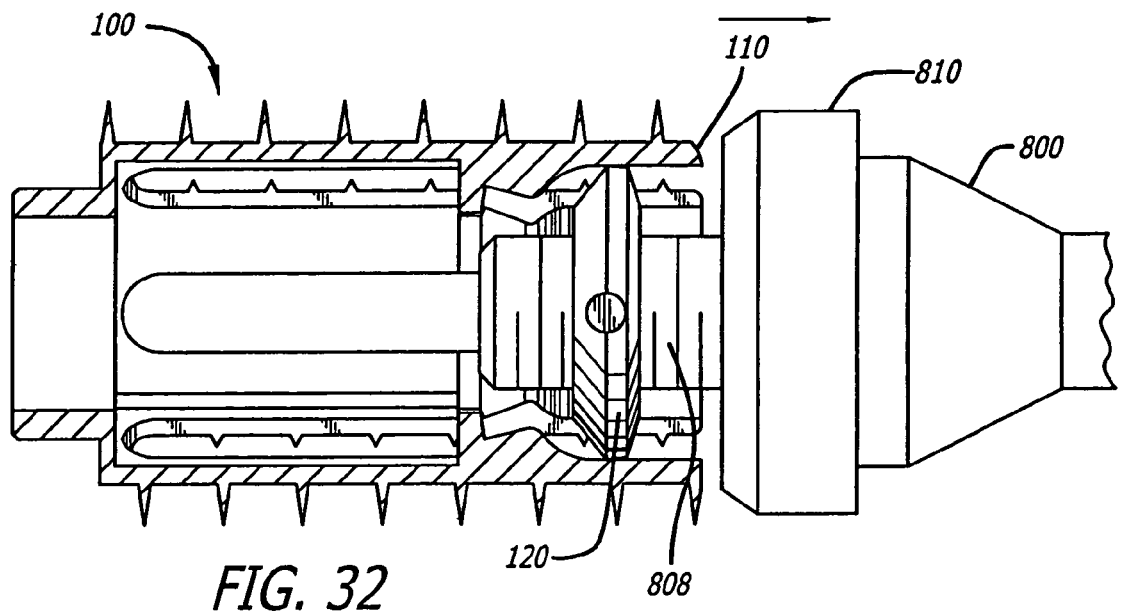
FIG. 32 is a partial side sectional view of the implant shown in FIG. 1 in a non-expanded state with the radial expander being removed from the leading end of the implant by the remover instrument of FIG. 30.

With reference to FIGS. 30-32, in certain circumstances, for example, where it may be desirable to revise an instrumentation and to access implant 100 from an anterior aspect of the spine, radial expander 120 may be removed from the leading end 104 (oriented near the anterior aspect of the space) of implant 100. FIG. 30 shows a remover 800 for removing radial expander 120 from hollow interior 103 of implant 100 through leading end 104. Remover 800 has a shaft 802, a distal end 804, and a proximal end 806. Distal end 804 has a threaded rod 808 and an enlarged head 810 with a diameter configured to enter hollow interior 103 of implant 100 in a radially expanded state and force apart arms 110. Proximal end 806 is preferably configured to be attached to a removable handle for rotating remover 800.

Threaded rod 808 of remover 800 threads into radial expander 120 causing forward movement of remover 800 toward leading end 104 of implant 100. As remover 800 moves toward leading end 104, enlarged head 810 contacts interior surface 114 of arms 110, forcing arms 110 to move outward and further away from the mid-longitudinal axis of implant 100. This movement in turn causes seat 118 to expand outward opening the entrance to seat 118, thus permitting radial expander 120 to be removed from seat 118 of implant 100. FIG. 32 shows remover 800 removing radial expander 120 from seat 118 to return arms 110 to their initial non-expanded position. The implant may then be removed from the implantation site if desired.

Figure 53:
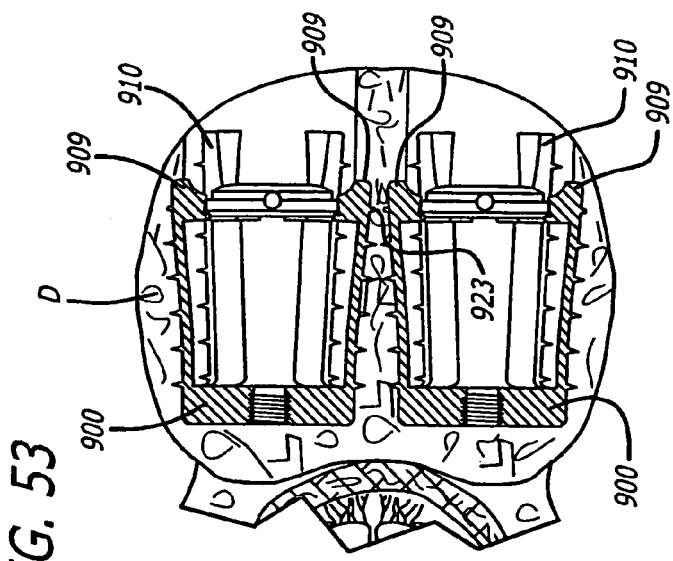
FIG. 53 is a fragmentary top plan view in partial cross section of a vertebra with two implants of FIG. 37 in an expanded state installed side-by-side into a disc space from an anterior approach with the trailing ends in closer proximity to each other than in FIG. 52A.

The method of the present invention may also be performed from an anterior approach to the spine. FIGS. 33-56 show various embodiments of an implant 900 for insertion from at least in part an anterior approach to the spine as well as instruments and the associated method for inserting and removing implant 900. Implant 900 is similar to implant 100, with certain differences noted below. As shown in FIGS. 33-36, implant 900 has an open trailing end 902, a leading end 904 shown closed in this embodiment, a base 905 proximate the leading end, and a shortened arm 909 and lengthened arms 910 extending from base 905. FIG. 37 shows an alternative embodiment of implant 900 having two opposed shortened arms 909 and lengthened arms 910. Shortened arms 909 are preferably located on at least one side of implant 900 when two implants are inserted side-by-side as shown in FIGS. 52A, 52B, and 53. Shortened arms 909 provide for a reduced diameter of trailing end 902 such that trailing end 902 does not substantially protrude from the disc space to minimize the risk of interference with delicate vascular and neurological structures present adjacent to the disc space. Shortened arms 909 also permit two implants 900 in an expanded state to be placed side-by-side in close proximity to each other in the disc space. Although a combination of shortened arms 909 and lengthened arms 910 is preferred, the invention is not so limited. For example, in situations where the surgeon determines it is appropriate, implant 900 may have arms 910 of generally equal length as shown in another alternative embodiment of implant 900 in FIG. 38.

The interaction between radial expander 920 and the interior surface of arms 909, 910 is similar to that between radial expander 120 and arms 110 (described in relation to FIGS. 9-11) except that unlike the interior surface of arm 110, shortened arms 909 have a notched area 917 that functions to hold the radial expander 920 in seat 918 and maintain shortened arms 909 in a radially expanded state when radial expander 920 is seated in seats 918 of lengthened arms 910.

In implant 900 a post 1000 is inserted through the trailing end 902. Leading end 904 preferably has a threaded opening 928 for threadably engaging post 1000. Post 1000 has a shaft 1002 with a first thread 1004 for cooperative engagement with a tool 1300 shown in FIG. 44 for pushing or otherwise moving radial expander 920 away from trailing end 902 and toward base 905 proximate leading end 904 of implant 900. Post 1000 has a head 1006 with a tool engagement area 1008 that is preferably hex-shaped to engage a post remover 1400 shown in FIG. 45, and a second thread 1010 shown in FIG. 50, 51 at the end opposite head 1006 for cooperative engagement with threaded opening 928 in leading end 904 of implant 900.

As an alternative to using a post with a threaded end for engagement with the leading end of the implant, a post may be used having a leading end with a retractable flange or other projection for cooperative engagement with the leading end of the implant. Such a post may then be used to rotate the radial expander into position in a fashion similar to that described with reference to FIGS. 23 and 24. Once the radial expander is seated, the flanges or other projections may be retracted, and the post may then be withdrawn.

As shown in FIGS. 33 and 39-41, radial expander 920 is similar to radial expander 120 shown in FIGS. 6-8. Opening 934 of radial expander 920 is preferably unthreaded. A threaded opening is not essential since radial expander 920 is moved by rotating tool 1300 and not by post 1000, described in more detail below.

FIG. 42 shows an implant driver 1100 for inserting implant 900 into a disc space. Driver 1100 has a shaft 1102 and a distal end 1104. Distal end 1104 preferably has an implant engaging head 1108 with flanges 1110 spaced apart by recessed areas and a bore 1120. Implant engaging head 1108 is preferably sized and shaped to cooperatively engage trailing end 902 of implant 900 for insertion into the disc space. Implant engaging head 1108 preferably is tapered to facilitate insertion into the interior of implant 900 and to facilitate the placement of flanges 1110 into spaces 912. Arms 909, 910 fit into recessed areas between flanges 1110. In this position, driver 1100 is engaged to implant 900 and can rotate implant 900. Bore 1120 is preferably configured to receive post 1000 so that driver 1100 may insert implant 900 with post 1000 already attached thereto.

FIG. 43 shows an implant holder 1200 for holding implant 900 in a stable position while one or more tools, for example rotating tool 1300, engages with post 1000 to move radial expander 920 toward leading end 904. Implant holder 1200 has a distal end 1202, a proximal end 1204, a shaft 1206 therebetween, and a handle 1208. Distal end 1202 preferably has a plurality of flanges 1210 that are configured for engagement with spaces 912 between arms 909, 910. Shaft 1206 is preferably hollow and sized to accommodate the passage of tools therethrough, for example, rotating tool 1300. Flanges 1210 are adapted to fit in spaces 912 between arms 909, 910 to hold implant 900. Rotating tool 1300 is used to rotate post 1000 to move radial expander 920 while implant 900 is held stable by holder 1200 to resist the rotational forces bearing upon post 1000.

FIG. 44 shows rotating tool 1300 for advancing radial expander 920 away from trailing end 902 and toward base 905 proximate leading end 904. Rotating tool 1300 has a distal end 1302 and a shaft 1310. Distal end 1302 has a bore 1312 with a thread 1314 adapted to cooperatively engage with first thread 1004 of post 1000. Bore 1312 preferably has an unthreaded portion at its leading end that permits rotating tool 1300 to move over a portion of post 1000 such as post head 1006 prior to engagement of the thread. As tool 1300 is rotated onto post 1000, distal end 1302 bears against radial expander 920 to advance radial expander 920 into implant 900. After radial expander 920 is seated into seat 918, rotating tool 1300 is unthreaded from post 1000 and removed from implant 900.

FIG. 45 shows a post remover 1400 for removing post 1000 after radial expander 920 has been seated in seat 918 of implant 900. Post remover 1400 has a shaft 1402 and a distal end 1404. Distal end 1404 has a bore 1406 with a post engagement surface 1408 that is preferably hex-shaped to cooperatively engage with tool engagement area 1008 of post 1000. Post remover 1400 removes post 1000 from implant 900 by unthreading post 1000 from opening 928 in leading end 904 of implant 900.

FIGS. 46-51 show various steps of a preferred method for inserting implant 900 from an anterior approach to the spine and using associated instrumentation disclosed herein.

Figure 46:
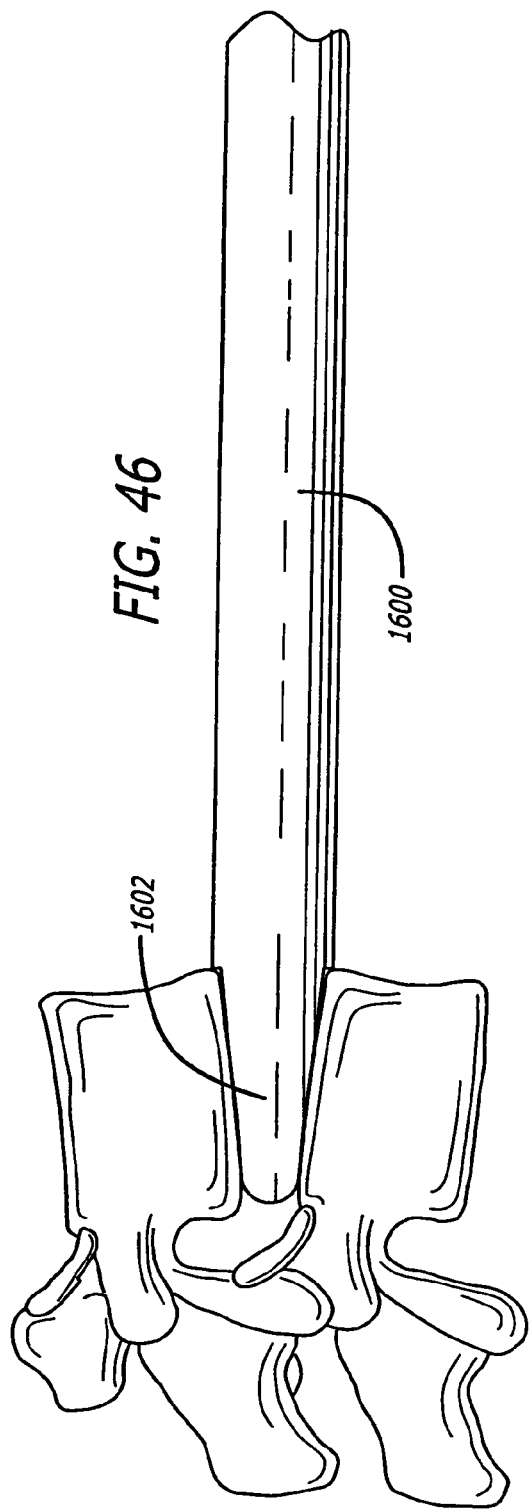
FIG. 46 is a side elevation view of two adjacent vertebrae and a hollow guard for use in preparing a disc space to receive the implant of FIG. 33.
Figure 47:
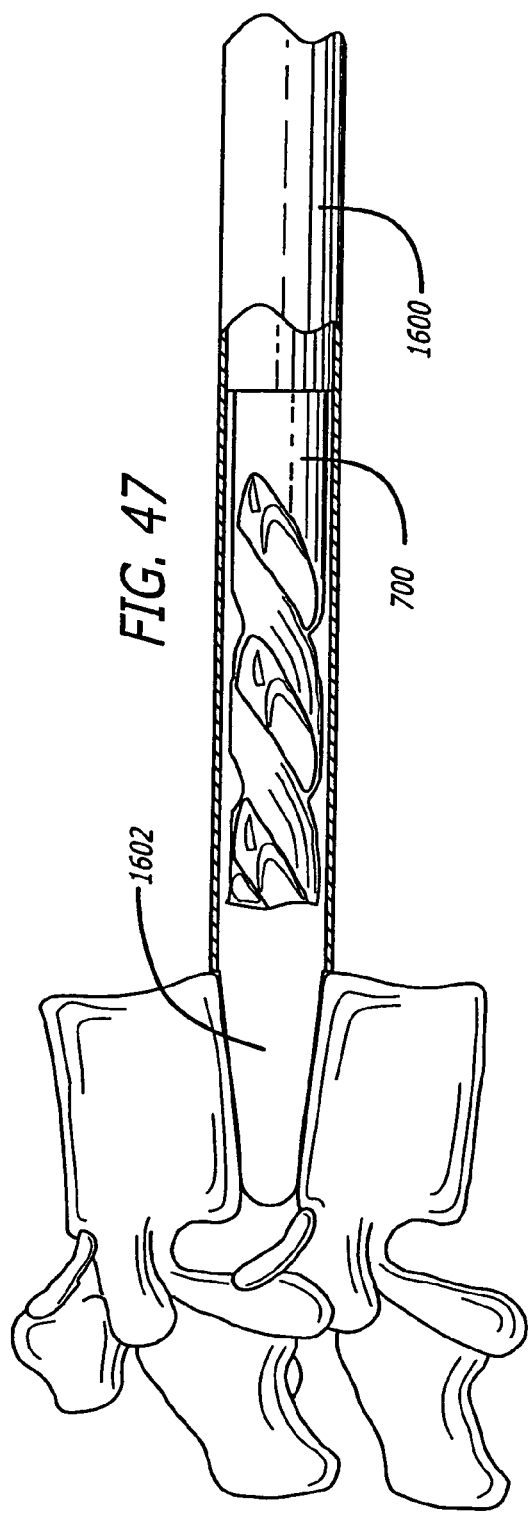
FIG. 47 is a side elevation view of the adjacent vertebrae and guard of FIG. 46 in partial cross-section and a side view of a drill being inserted through the guard.

FIGS. 46 and 47 show insertion of a guard 1600 with disc penetrating extensions 1602 into the disc space and the use of drill 700 to prepare the disc space for implantation. Disc penetrating extensions 1602 need not be but are preferably angled to place the adjacent vertebral bodies in angular relationship to each other. As taught in U.S. Pat. No. 6,080,155 to Michelson incorporated by reference herein, the guard may have one or more extensions of any size or shape suitable for the intended purpose and one or more bores which could, but need not, be in part overlapping. It is understood that the use of such a guard is only preferred and not required. The guard may be of any type suitable for the purpose of providing protected access while the disc space is prepared and during implantation including, but not limited to, the guards incorporated by reference above.

Figure 48:
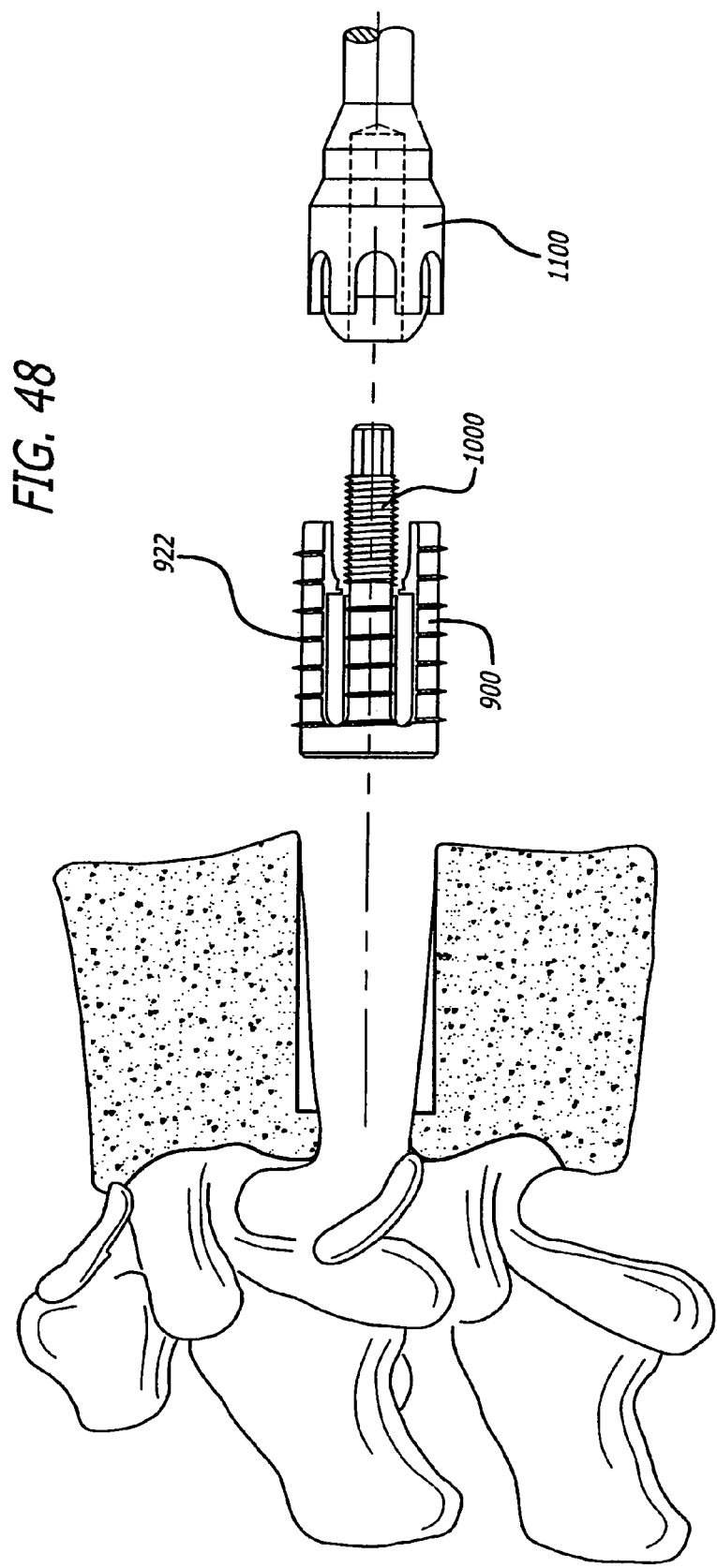
FIG. 48 is an exploded side view of the implant of FIG. 33, the instrument of FIG. 42, and an implant receiving space formed across the height of the disc space and the adjacent vertebral bodies shown in partial cross section.

In FIG. 48, drill 700 and guard 1600 are withdrawn and driver 1100 is used to insert implant 900 into the prepared disc space. In this example, implant 900 is rotatably inserted so that thread 922 penetrably engages the bone of the adjacent vertebral bodies. At the option of the surgeon, guard 1600 may be left in place throughout the whole procedure, the procedure then being carried out through the hollow shaft of guard 1600. Additionally, implant 900 may be installed without first installing post 1000 into implant 900. However, it is preferred that post 1000 is installed in implant 900 before implant 900 is installed into the disc space.

Figure 49:
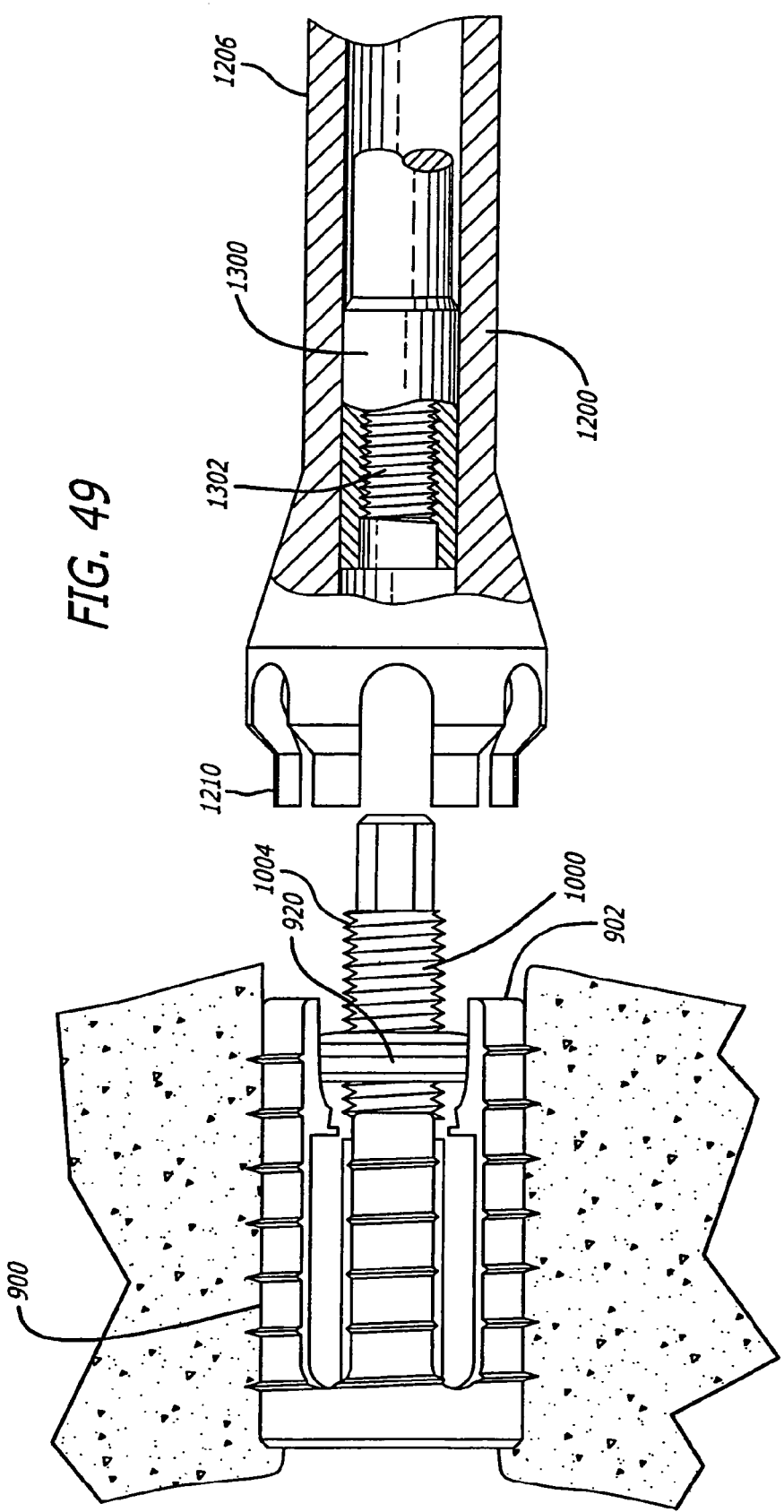
FIG. 49 is a side elevation view of the implant of FIG. 33 in a non-expanded state inserted into the implant receiving space formed across the height of the disc space and two adjacent vertebral bodies in cross section and a fragmentary view of the instrument of FIG. 43 in partial cross section being positioned to engage the arms of the implant with the instrument of FIG. 44 shown in partial cross section being inserted therethrough for cooperative engagement with the post.
Figure 50:
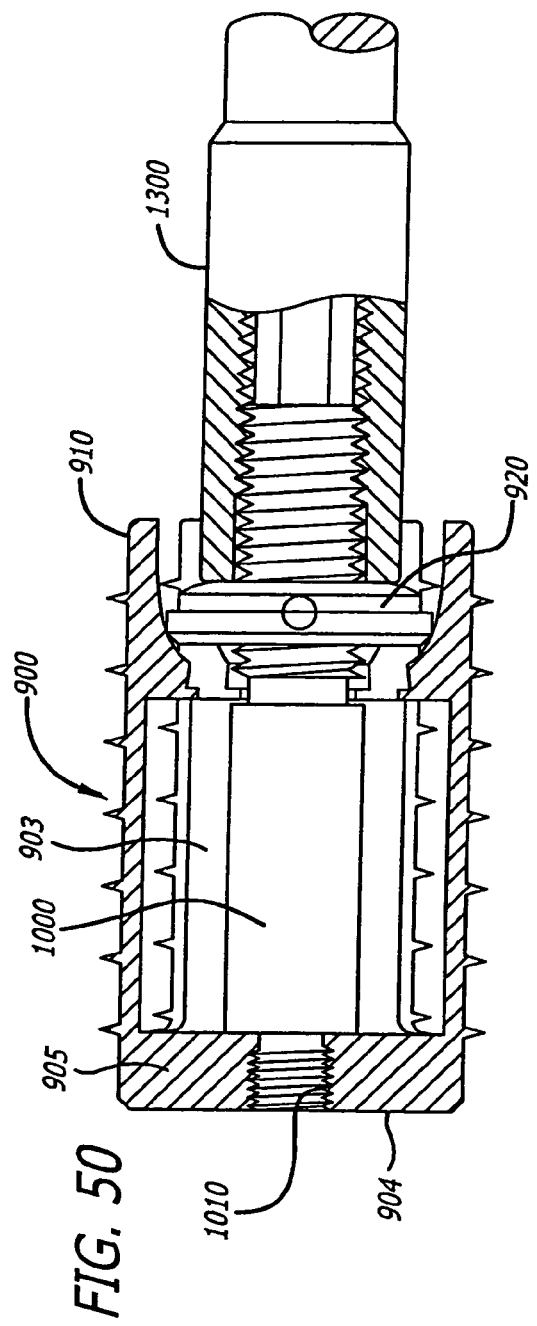
FIG. 50 is a side elevation view in partial cross section of the implant of FIG. 33 with the instrument of FIG. 44 in rotational engagement with the post of FIG. 33 moving the radial expander into the implant.

As illustrated in FIG. 49, radial expander 920 is moved onto post 1000 and implant holder 1200 is moved into position. After flanges 1210 of implant holder 1200 are engaged with arms 909, 910 of implant 900, rotating tool 1300 is inserted through the interior of shaft 1206 so that threaded bore 1302 of rotating tool 1300 cooperatively engages first thread 1004 of post 1000. As shown in FIG. 50, after rotating tool 1300 and post 1000 are rotationally engaged, continued rotation of rotating tool 1300 linearly forces radial expander 920 away from trailing end 902 and to bear against the interior surfaces of arms 909, 910, causing arms 909, 910 to be forced away from the mid-longitudinal axis of the implant as described above in relation to implant 100 and FIGS. 9-11.

Figure 51:
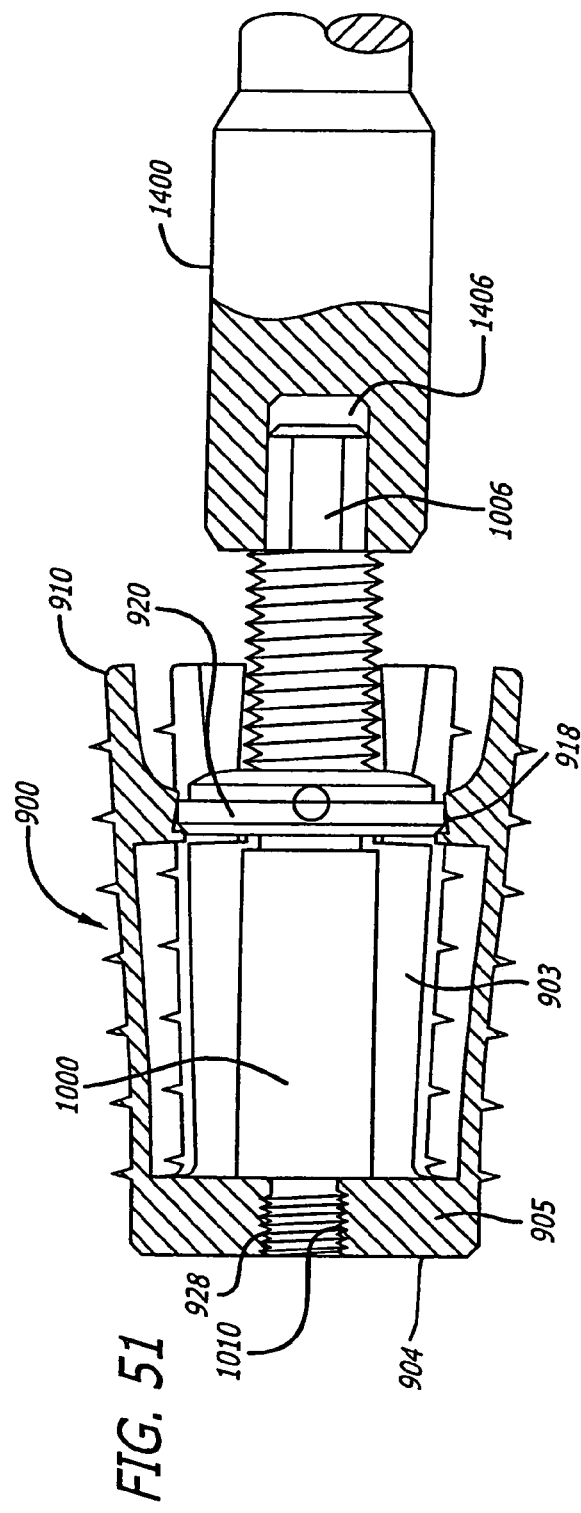
FIG. 51 is a side elevation view in partial cross section of the implant of FIG. 33 with the instrument of FIG. 45 being used to remove the post of FIG. 33 from the implant in the expanded state.
Figure 52A:
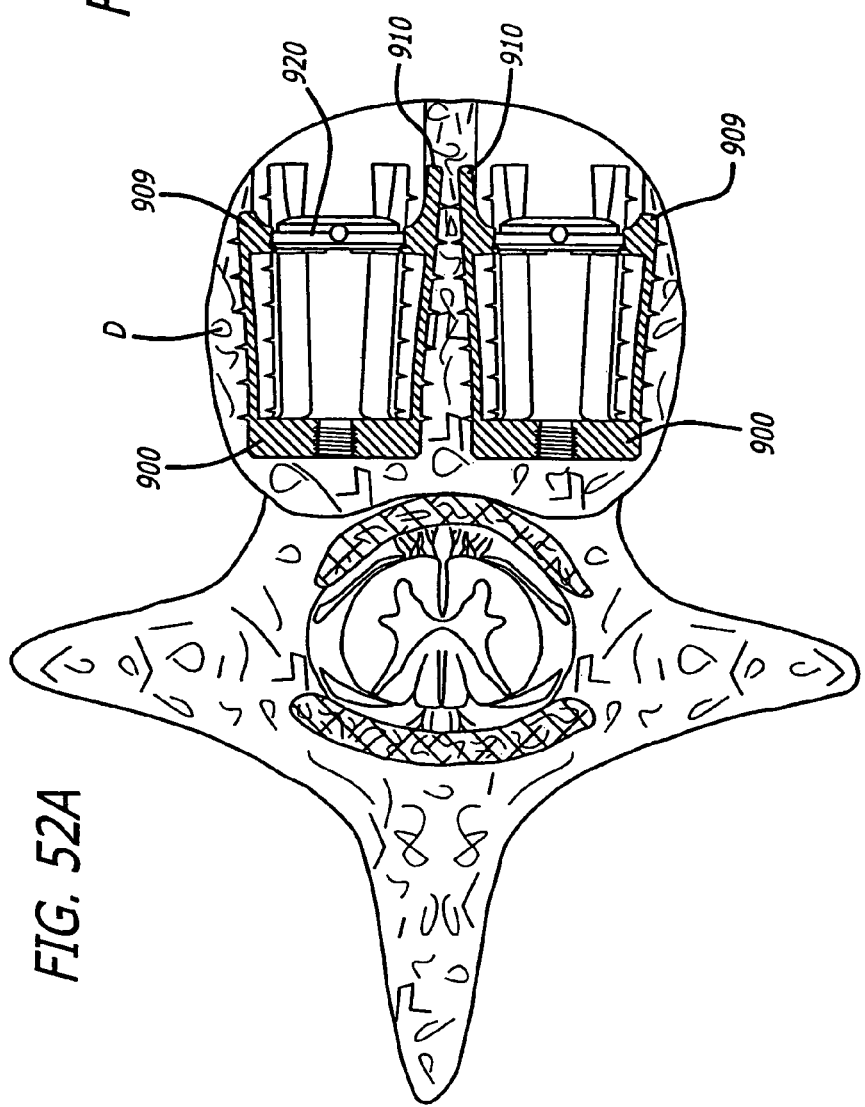
FIG. 52A is a top plan view in partial cross section of a vertebra with two implants of FIG. 33 in an expanded state installed side-by-side into a disc space from an anterior approach with the trailing ends in close proximity to each other and the shortened arms oriented toward the antero-lateral aspects of the vertebral body.
Figure 52B:
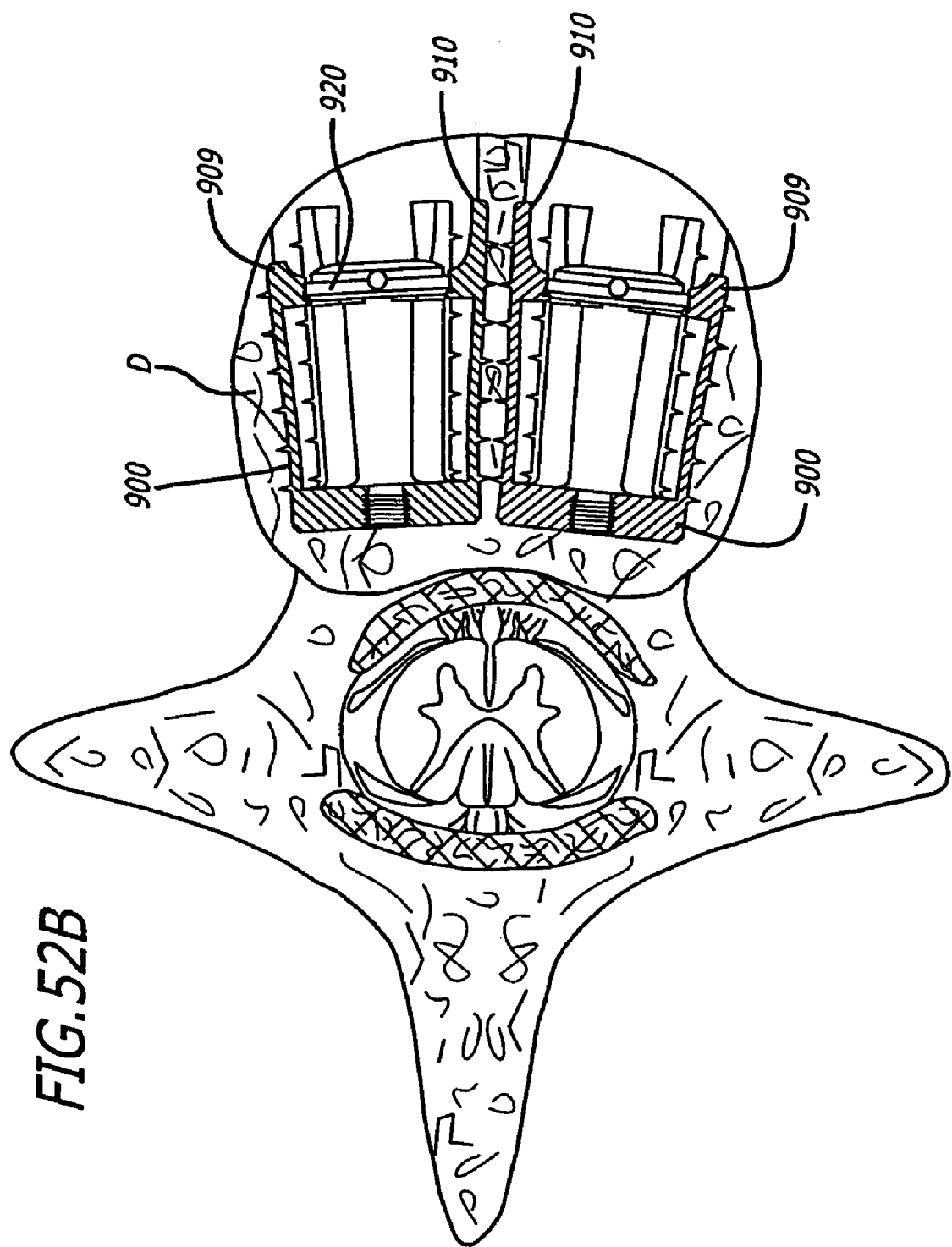
FIG. 52B is a top plan view in partial cross section of a vertebra with two implants of FIG. 33 in an expanded state installed side-by-side into a disc space from an anterior approach with the trailing ends in close proximity to each other in a toed-in orientation and the shortened arms oriented toward the antero-lateral aspects of the vertebral body.

As shown in FIG. 51, after radial expander 920 is seated into seat 918 and implant 900 is placed in an expanded state, post remover 1400 is used to engage head 1006 of post 1000. Rotating post remover 1400 disengages post 1000 from threaded opening 928 of implant 900, allowing post 1000 to be withdrawn through opening 934 of radial expander 920 and from the interior of the implant.

Figure 33:
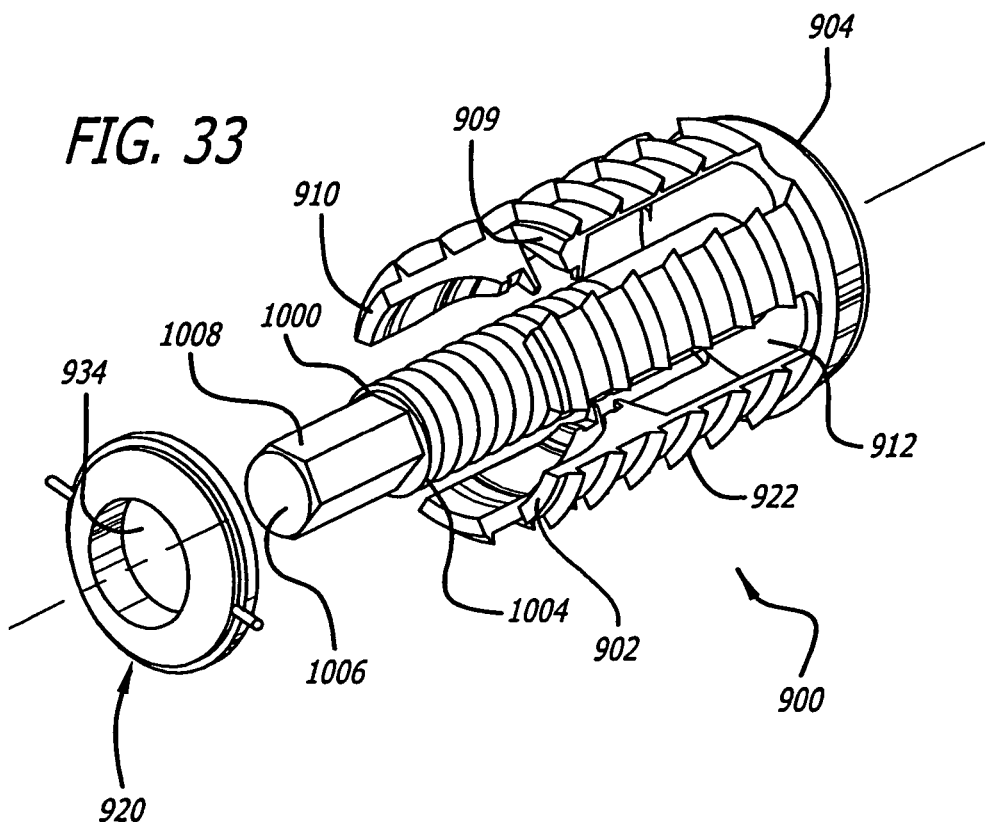
FIG. 33 is an exploded perspective view of a spinal fusion implant, radial expander, and threaded post in accordance with another preferred embodiment of the present invention for anterior insertion into the spine.
Figure 39:
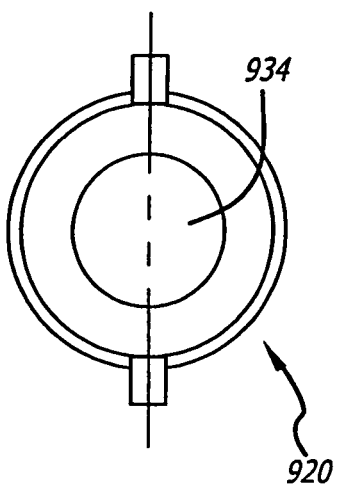
FIG. 39 is a trailing end elevation view of the radial expander of FIG. 33.
Figure 40:
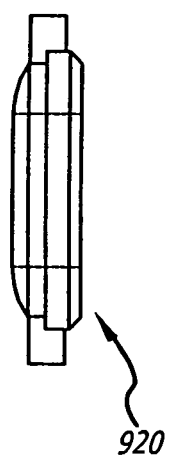
FIG. 40 is a side elevation view of the radial expander of FIG. 33.
Figure 41:
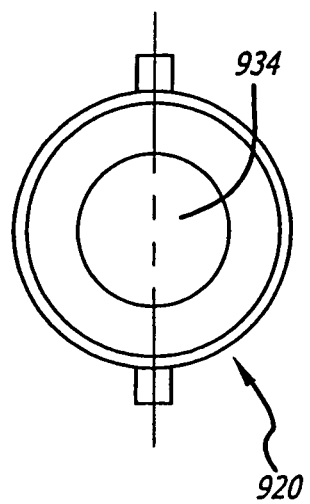
FIG. 41 is a leading end elevation view of the radial expander of FIG. 33.

FIGS. 52A, 52B, and 53 show two implants 900 in a radially expanded state placed in close proximity to one another within the perimeter of a disc space D. In FIG. 52A and 52B, implants 900 of FIG. 33 are preferably positioned such that shortened arms 909 face the antero-lateral aspect of the vertebral bodies such that the structure of each implant is kept substantially within the disc space to minimize the risk of interference with delicate vascular and neurological structures present adjacent to the disc space. In FIG. 52B, implants 900 are oriented toward each other in a toed-in configuration permitting the implants to be closer to each other in a side-by-side placement. Such placement permits the use of larger implants to better fill the disc space than may be possible with implants positioned parallel to each other.

In FIG. 53, two implants 900 of FIG. 37, each having opposed shortened arms 909, are preferably placed such that the mid-longitudinal axis of each implant are in closer proximity to one another than the embodiment shown in FIG. 52A. Closer placement is made possible, by way of example only, by positioning each implant such that shortened arms 909 face each other within the disc space. Additionally, the size of thread 922 may be reduced towards trailing end 902 so that trailing end 902 has a reduced thread portion 923 to minimize contact with the thread of an adjacent implant. Such an orientation permits greater expansion to occur without a lengthened arm from one implant crossing the lengthened arm of an implant adjacent thereto. In all the embodiments described herein, it should be apparent that a number of arrangements of shortened and/or lengthened arms are possible and all within the broad scope of the present invention.

Figure 55:
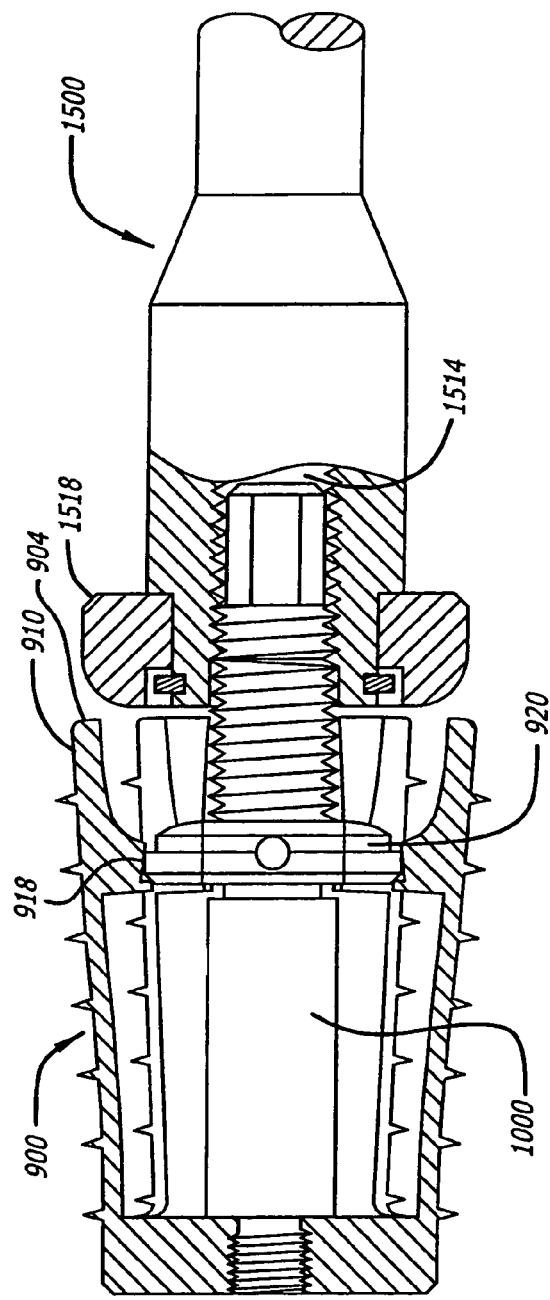
FIG. 55 is a partial side sectional view of the implant of FIG. 33 and the instrument of FIG. 54 being used to unlock the radial expander.
Figure 56:
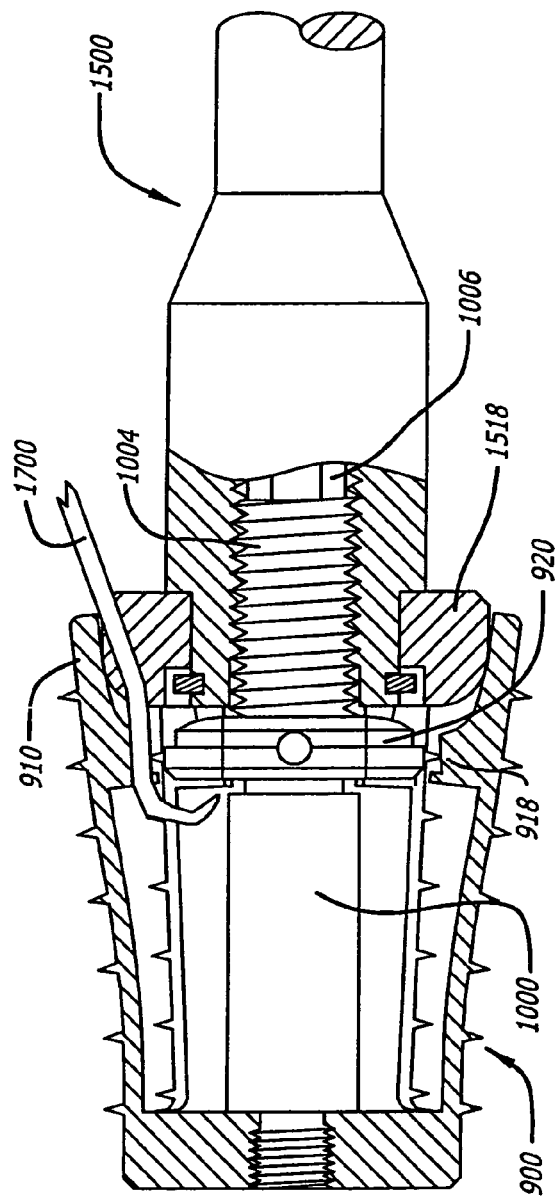
FIG. 56 is a partial side sectional view of the implant of FIG. 33 with the instrument of FIG. 54 being fully deployed in the implant and a hook being used to extract the radial expander from the implant.

FIGS. 54-56 show a preferred remover and methods of disengaging radial expander 920 from seat 918 of implant 900 if it is desired to uninstall implant 900. FIG. 54 shows a remover 1500 for removing radial expander 920 from hollow interior 903 of implant 900 through trailing end 902. Remover 1500 has a shaft 1502 and a distal end 1504. Distal end 1504 has a bore 1514 with a thread 1516 that is configured for cooperative engagement with first thread 1004 of post 1000, a collar 1518 with an outer diameter slightly smaller than the diameter of hollow interior 903 of implant 900 in a radially expanded state, and a bearing 1520 that allows remover 1500 to rotate relative to collar 1518. Bore 1514 preferably has an unthreaded portion at its leading end that permits remover 1500 to move over a portion of post 1000 prior to rotational engagement.

As shown in FIGS. 55 and 56, threaded bore 1514 of remover 1500 threads onto post 1000 causing forward movement of remover 1500 into trailing end 904 of implant 900. As remover 1500 moves into trailing end 904, collar 1518 contacts arms 909, 910, forcing arms 909, 910 to move outward away from the mid-longitudinal axis of the implant. This movement in turn causes seat 918 to expand outward to release radial expander 920, thus permitting radial expander 920 to be removed from implant 900.

FIG. 56 shows an instrument, for example a hook 1700, for removing radial expander 920 from implant 900 to return arms 909, 910 to their initial or non-expanded position.

The implants described herein preferably have a generally circular cross section transverse to the mid-longitudinal axis of the implant. In the collapsed position, the implants may have a generally cylindrical configuration or may be in the shape of a cylinder with at least a portion of a side removed. The implants may be tapered from trailing end to leading end and may have a generally frusto-conical configuration in the collapsed position to facilitate insertion into the implantation space.

In another embodiment, in the expanded position, the implants described herein may have a leading end or a trailing end tapered at an angle that matches the angle of the upper, lower, and side portions in the expanded position.

The radially expandable spinal fusion implant may include, be made of, treated, coated, filled, used in combination with, or have a hollow for containing artificial or naturally occurring materials and/or substances suitable for implantation in the human spine. These materials and/or substances include any source of osteogenesis, bone growth promoting materials, bone, bone derived substances or products, demineralized bone matrix, ossifying proteins, bone morphogenetic proteins, hydroxyapatite, genes coding for the production of bone, and bone including, but not limited to, cortical bone. The implant can also be formed of an artificial material stronger than bone such as metal including, but not limited to, titanium and its alloys, surgical grade plastics, plastic composites, ceramics, or other materials suitable for use as a spinal fusion implant. The implant can include at least in part of materials that are bioabsorbable and/or resorbable in the body such as bone and/or bone growth promoting materials. The implant of the present invention can be formed of a porous material or can be formed of a material that intrinsically participates in the growth of bone from one of adjacent vertebral bodies to the other of adjacent vertebral bodies. Where such implants are for posterior implantation, the trailing ends of such implants may be treated with, coated with, or used in combination with chemical substances to inhibit scar tissue formation in the spinal canal. The implants of the present invention may be adapted to facilitate the electrostimulation of the fusion area into which they are inserted and the proximate bone thereabout. The implant of the present invention may be modified, or used in combination with materials to make it antibacterial, such as, but not limited to, electroplating or plasma spraying with silver ions or other substance. At least a portion of the implant may be treated to promote bone ingrowth between the implant and the adjacent vertebral bodies. The implant of the present invention may be used in combination with spinal fixation hardware, bone screws, plates, rods, tethers of synthetic chords or wires.

Although various embodiments of the present invention have been disclosed, they are but preferred embodiments for the purpose of illustration by example and not limitation. It should be understood that any modifications of these teachings as would be known to one of ordinary skill in the art are anticipated and within the scope of the present inventive teachings.

What is claimed is:

1. An orthopedic implant for implantation at least in part between two adjacent bone masses, said implant comprising:
    a body having a leading end, a trailing end opposite said leading end, a mid-longitudinal axis, and a length between said leading and trailing ends of said body, said body having a mid-point bisecting the length of said body, said body having a first side portion adapted to contact one of the adjacent bone masses, a second side portion opposite said first side portion adapted to contact another one of the adjacent bone masses, and at least a third side portion between said first and second side portions, each of said first, second, and third side portions extending from said trailing end of said body and being spaced apart from one another to form a hollow interior therebetween, said hollow interior being configured to hold at least some bone growth promoting material therein, each of said first, second, and third side portions configured to move at least in part in a direction away from the mid-longitudinal axis of the body allowing for expansion of said body in at least three directions, said first, second, and third side portions having a collapsed position and an expanded position; and an expander at least in part within said hollow interior, said expander configured to cooperatively engage an instrument adapted to be inserted through said trailing end of said body to engage and to move said expander from a position proximate said leading end when said body is in the collapsed position away from said leading end and toward said trailing end of said body to place said body in the expanded position, said, expander adapted, to contact and to move said first, second, and third side portions away from the mid-longitudinal axis of said body, said first, second, and third side portions of said body adapted to cooperatively engage said expander to locate said expander at a fixed position along the length of said body, said fixed position being closer to the mid-point of said implant than to said leading end of said implant, said first, second, and third side portions of said body adapted to resist dislodgment of said expander from that location when said implant is in the expanded position, said expander adapted to hold at least a portion of said first, second, and third side portions apart so as to maintain the expanded position of said body and to resist the collapse of said body to the collapsed position when said body is in the expanded position, when said body is in the expanded position said hollow interior being substantially unobstructed by any mechanism to move said expander so as to permit growth of bone through a portion of said hollow interior between said expander and said trailing end and through a portion of said hollow interior between said expander and said leading end of said body.

2. The implant of claim 1, wherein said expander includes a threaded opening for threadable engagement with said instrument used to move said expander from an initial position to a final position to place said body in the expanded position.

3. The implant of claim 1, wherein each of said first, second, and third side portions are configured to permit said expander to seat therein in at least said expanded position.

4. The implant of claim 1, wherein at least a portion of said first, second, and third side portions are separated by a space, said expander includes at least one guide peg extending therefrom and configured to be placed in said space between at least a portion of at least one of said first, second, and third side portions.

5. The implant of claim 1, wherein at least one of said first, second, and third side portions comprises a plurality of arms separated from one another at least in part by a space, said space being at least one of an opening, slit, and slot.

6. The implant of claim 5, wherein said arms are of different lengths.

7. The implant of claim 5, wherein said arms are aligned parallel with the mid-longitudinal axis of said body in the collapsed position.

8. The implant of claim 1, wherein at least one of said first, second, and third side portions has an interior surface, at least a portion of said interior surface forming a ramp adapted to contact said expander.

9. The implant of claim 1, wherein at least one of said first, second, and third side portions has an interior surface, at least a portion of said interior surface forming a seat adapted to receive and locate said expander along the length of said body.

10. The implant of claim 1, wherein at least one of said first, second, and third side portions is sufficiently resilient so as to bend to be moved away from said mid-longitudinal axis of said body.

11. The implant of claim 1, wherein said first, second, and third side portions when said implant is in the collapsed position form a generally cylindrical shape.

12. The implant of claim 1, further in combination with said instrument, said instrument including a post adapted to be inserted at least in part within said hollow interior of said body for moving said expander along at least a portion of the length of said body between said first and second side portions of said implant, said post having a shaft with a first end adapted to be coupled to one of said leading and trailing ends of said body and a second end opposite said first end configured to cooperatively engage a tool used for inserting said post into said body.

13. The implant of claim 12, wherein said shaft is at least in part threaded and said expander has a threaded opening configured to threadably engage said shaft so that rotation of said post within said body moves said expander along at least a portion of the length of said body to force apart said first, second, and third side portions.

14. The implant of claim 13, wherein said threaded part of said shaft of said post extends a distance greater along said shaft than the depth of said threaded opening of said expander.

15. The implant of claim 1, wherein said trailing end of said body includes at least one non-threaded opening.

16. The implant of claim 1, further comprising a bone engaging surface formed on the exterior of at least said first, second, and third side portions for engaging the adjacent bone masses, said bone engaging surface including at least one of a thread, a ratchet, a spline, surface roughenings, and knurling.

17. The implant of claim 1, wherein said implant comprises an artificial material other than bone.

18. The implant of claim 1, further comprising a thread formed on the exterior of at least said first, second, and third side portions for engaging the adjacent bone masses, said thread extending continuously around the mid-longitudinal axis of said implant for at least one complete turn.

19. The implant of claim 1, wherein said trailing end of said implant has a constant cross section transverse to the mid-longitudinal axis in both the collapsed and expanded positions.

20. The implant of claim 1, wherein each of said first, second, and third side portions has a free end at said leading end of said implant.

21. An orthopedic implant for implantation at least in part between two adjacent bone masses, said implant comprising:
a body having a leading end, a trailing end opposite said leading end, a mid-longitudinal axis, and a length between said leading and trailing ends of said body, said body having a mid-point bisecting the length of said body, said body having a first side portion adapted to contact one of the adjacent bone masses, a second side portion opposite said first side portion adapted to contact another one of the adjacent bone masses, and at least a third side portion between said first and second side portions, each of said first, second, and third side portions extending from said trailing end of said body and being spaced apart from one another to form a hollow interior therebetween, each of said first, second, and third side portions configured to move at least in part in a direction away from the mid-longitudinal axis of the body allowing for expansion of said body in at least three directions, said first, second, and third side portions having a collapsed position and an expanded position;

an expander at least in part within said hollow interior, said expander configured to cooperatively engage an instrument adapted to be inserted through said trailing end of said body to engage and to move said expander from a position proximate said leading end when said body is in the collapsed position away from said leading end and toward said trailing end of said body to place said body in the expanded position, said expander adapted to contact and to move said first, second, and third side portions away from the mid-longitudinal axis of said body, said first, second, and third side portions of said body adapted to cooperatively engage said expander to locate said expander at a fixed position along the length of said body, said fixed position being closer to the mid-point of said implant than to said leading end of said implant, said first, second, and third side portions of said body adapted to resist dislodgment of said expander from that location when said implant is in the expanded position, said expander adapted to hold at least a portion of said first, second, and third side portions apart so as to maintain the expanded position of said body and to resist the collapse of said body to the collapsed position when said body is in the expanded position; and a bone growth promoting material, said hollow interior being configured to hold at least some of the bone growth promoting material therein.

22. The implant of claim 21, wherein said bone growth promoting material is selected from one of bone, bone derived products, demineralized bone matrix, ossifying proteins, bone morphogenetic protein, hydroxyapatite, and genes coding for the production of bone.

23. An orthopedic implant for implantation at least in part between two adjacent bone masses, said implant comprising:

a body having a leading end, a trailing end opposite said leading end, a mid-longitudinal axis, and a length between said leading and trailing ends of said body, said body having a mid-point bisecting the length of said body, said body having a first side portion adapted to contact one of the adjacent bone masses, a second side portion opposite said first side portion adapted to contact another one of the adjacent bone masses, and at least a third side portion between said first and second side portions, each of said first, second, and third side portions extending from said trailing end of said body and being spaced apart from one another to form a hollow interior therebetween, said hollow interior being configured to hold at least some bone growth promoting material therein, each of said first, second, and third side portions configured to move at least in part in a direction away from the mid-longitudinal axis of the body allowing for expansion of said body in at least three directions, said first, second, and third side portions having a collapsed position and an expanded position; and an expander at least in part within said hollow interior, said expander configured to cooperatively engage an instrument adapted to be inserted through said trailing end of said body to engage and to move said expander from a position proximate said leading end when said body is; in the collapsed position away from said leading end and toward said trailing end of said body to place said body in the expanded position, said expander adapted to contact and to move said first, second, and third side portions away from the mid-longitudinal axis of said body, said first, second, and third side portions of said body adapted to cooperatively engage said expander to locate said expander at a fixed position along the length of said body, said fixed position being closer to the mid-point of said implant than to said leading end of said implant, said first, second, and third side portions of said body adapted to resist dislodgment of said expander from that location when said implant is in the expanded position, said expander adapted to hold at least a portion of said first, second, and third side portions apart so as to maintain the expanded position of said body and to resist the collapse of said body to the collapsed position when said body is in the expanded position, wherein said implant is at least in part resorbable.

* * * * *